(12) United States Patent
Huibregtse et al.

(10) Patent No.: US 9,322,787 B1
(45) Date of Patent: Apr. 26, 2016

(54) GLASS CONTAINER INSPECTION MACHINE WITH A GRAPHIC USER INTERFACE

(71) Applicant: Emhart Glass S.A., Cham (CH)

(72) Inventors: David Huibregtse, Pinellas Park, FL (US); Joseph M. Fradley, St. Petersburg, FL (US); Jakob A. Driscoll, Tampa, FL (US)

(73) Assignee: Emhart Glass S.A., Cham (CH)

( * ) Notice: Subject to any disclaimer, the term of this patent is extended or adjusted under 35 U.S.C. 154(b) by 87 days.

(21) Appl. No.: 14/517,806

(22) Filed: Oct. 18, 2014

(51) Int. Cl.
| | |
|---|---|
| G06K 9/00 | (2006.01) |
| G01N 21/88 | (2006.01) |
| G01N 21/90 | (2006.01) |
| G01N 21/958 | (2006.01) |
| G06F 3/041 | (2006.01) |
| G06F 3/0485 | (2013.01) |
| G06F 3/0488 | (2013.01) |
| G01N 21/84 | (2006.01) |

(52) U.S. Cl.
CPC .......... *G01N 21/8851* (2013.01); *G01N 21/909* (2013.01); *G01N 21/9036* (2013.01); *G01N 21/958* (2013.01); *G06F 3/0412* (2013.01); *G06F 3/0485* (2013.01); *G06F 3/04883* (2013.01); *G01N 2021/845* (2013.01); *G01N 2021/8883* (2013.01)

(58) Field of Classification Search
CPC .............. G01N 2021/845; G01N 2021/8883; G01N 21/8851; G01N 21/9036; G01N 21/909; G06F 3/0412
See application file for complete search history.

(56) References Cited

U.S. PATENT DOCUMENTS

| | | |
|---|---|---|
| 5,354,984 A | 10/1994 | Baldwin |
| 5,436,722 A | 7/1995 | Baldwin |
| 5,486,692 A | 1/1996 | Baldwin |
| 5,495,330 A | 2/1996 | Champaneri et al. |
| 5,917,602 A | 6/1999 | Bonewitz et al. |
| 5,923,419 A | 7/1999 | Thomas |
| 6,031,221 A | 2/2000 | Furnas |
| 6,618,495 B1 | 9/2003 | Furnas |
| 6,793,067 B1 | 9/2004 | Raupp |
| 6,795,176 B1 | 9/2004 | Tennakoon et al. |
| 6,915,894 B2 | 7/2005 | Raupp |
| 6,989,857 B2 | 1/2006 | Furnas |
| 7,120,284 B2 | 10/2006 | Furnas |
| 7,256,389 B2 | 8/2007 | Prasad |
| 7,781,723 B1 | 8/2010 | Furnas |
| 7,816,639 B2 | 10/2010 | Diehr et al. |
| 8,058,607 B2 | 11/2011 | Diehr et al. |
| 2002/0063215 A1* | 5/2002 | Yagita ................ G01N 21/9027 250/341.1 |
| 2011/0141265 A1* | 6/2011 | Holtkamp .............. G01J 5/0003 348/86 |
| 2015/0076353 A1* | 3/2015 | Bathelet ................ B07C 5/3408 250/340 |

* cited by examiner

*Primary Examiner* — Gregory M Desire
(74) *Attorney, Agent, or Firm* — Reinhart Boerner Van Deuren s.c.

(57) ABSTRACT

An improved system and method for automatically glass containers for defects and facilitates the identification and review of extensive information on defects identified by the glass container inspection machine on a touchscreen monitor. User gestures are used to review images larger than a size that can be displayed at any given time on the touchscreen monitor, to access and display images of glass containers having parameters that vary from the predetermined parameters, and to setup glass container inspection machine parameters and details of the inspections.

20 Claims, 19 Drawing Sheets

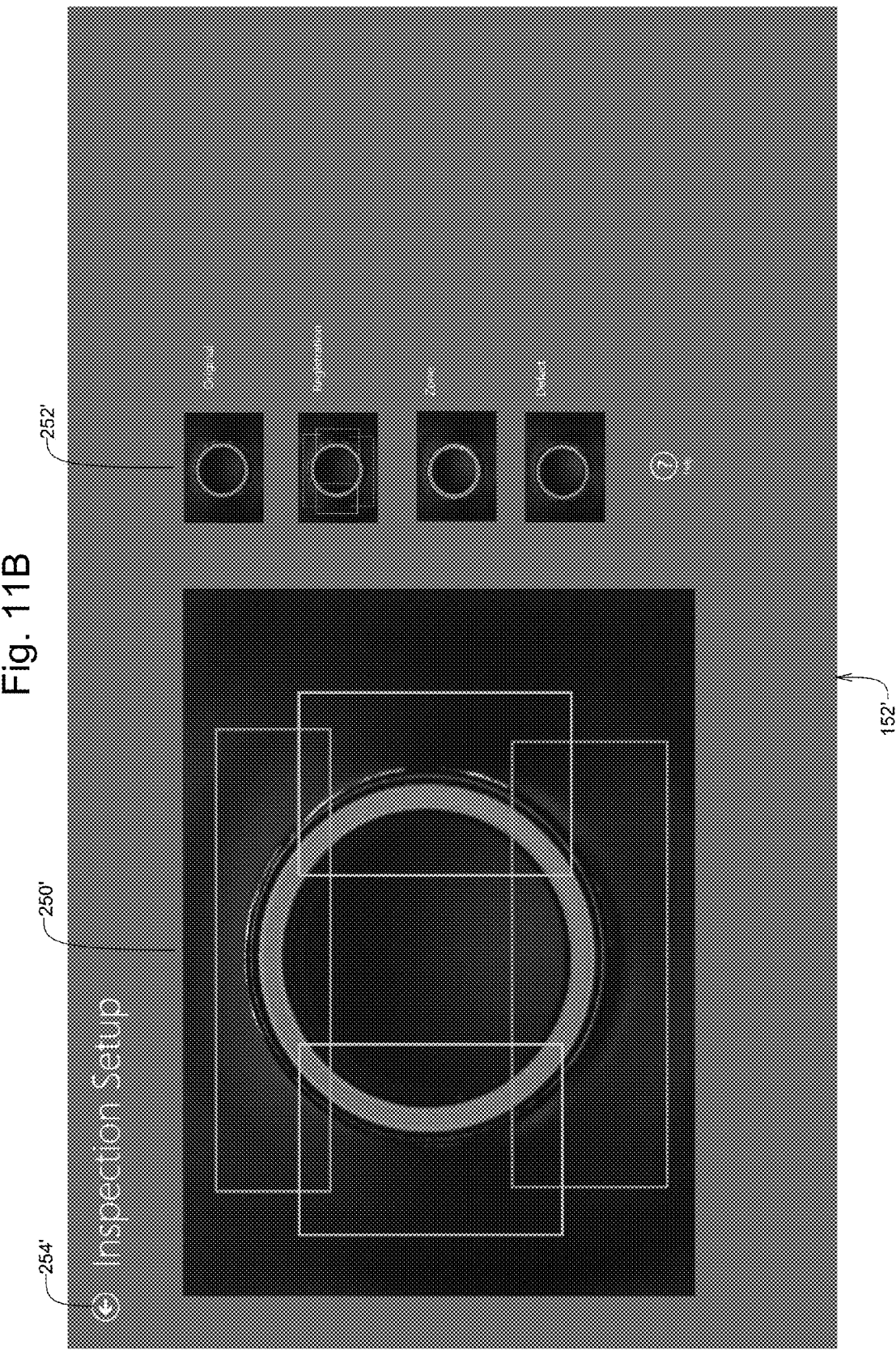

GLASS CONTAINER INSPECTION MACHINE WITH A GRAPHIC USER INTERFACE

BACKGROUND OF THE INVENTION

Field of the Invention

The present invention relates generally to machines that inspect glass containers (bottles) for defects, and more particularly to an glass container inspection system and method having a graphic user interface that may be used to review and obtain extensive information on defects identified by the glass container inspection system.

Glass containers are made in a manufacturing process that has three parts, namely the batch house, the hot end, and the cold end. The batch house is where the raw materials for glass (which may typically include sand, soda ash, limestone, cullet (crushed, recycled glass), and other raw materials) are prepared and mixed into batches. The hot end begins with a furnace, in which the batched materials are melted into molten glass, and from which a stream of molten glass flows.

The molten glass is cut into cylinders of glass called gobs, which fall by gravity into blank molds. In the blank molds, a pre-container referred to as a parison is formed, either by using a metal plunger to push the glass into the blank mold, or by blowing the glass from below into the blank mold. The parison is inverted and transferred to a mold, where the parison is blown out into the shape of the container. The hot end also includes an annealing process which prevents the containers from having weakened glass caused by stresses caused by uneven cooling. The annealing process is used to achieve even cooling, using an annealing oven or Lehr to heat the containers, and then slowly cool them over a twenty to sixty minute period.

The role of the cold end of the glass container manufacturing process is inspection of the containers to ensure that they are of acceptable quality. All glass containers are inspected by automated machines after manufacturing for a variety of faults, typically including small cracks in the glass referred to as checks, foreign inclusions referred to as stones, bubbles in the glass referred to as blisters, and excessively thin walls. An example of one such inspection is taught in U.S. Pat. No. 6,031,221, to Furnas, which patent is assigned to the assignee of the present patent application, and which patent is hereby incorporated herein by reference in its entirety. In addition, inspectors carry out a number of checks manually on samples of the containers, which commonly include visual and dimensional checks.

Since these inspections are performed as part of a large scale manufacturing process, those skilled in the art will appreciate that it must be performed at high speed, for example at an inspection rate of approximately 200 to 1000 glass containers per minute. Thus, in the space of approximately 60 to 300 milliseconds, a glass container must have been brought into an inspection station, have a full inspection process performed on the glass container, and removed from the inspection station as another glass container is brought into the inspection station.

Other relevant inspection machine patents include U.S. Pat. No. 5,354,984, to Baldwin; U.S. Pat. No. 5,436,722, to Baldwin; U.S. Pat. No. 5,486,692, to Baldwin; U.S. Pat. No. 5,495,330, to Champaneri et al.; U.S. Pat. No. 5,917,602, to Bonewitz et al.; U.S. Pat. No. 5,923,419, to Thomas et al.; U.S. Pat. No. 6,618,495, to Furnas; U.S. Pat. No. 6,793,067, to Raupp; U.S. Pat. No. 6,795,176, to Tennakoon et al.; U.S. Pat. No. 6,915,894, to Raupp; U.S. Pat. No. 6,989,857, to Diehr; U.S. Pat. No. 6,989,857, to Furnas; U.S. Pat. No. 7,120,284, to Furnas; U.S. Pat. No. 7,256,389, to Masud; U.S. Pat. No. 7,781,723, to Furnas.; U.S. Pat. No. 7,816,639, to Diehr et al.; and U.S. Pat. No. 8,058,607, to Diehr et al., which patents are assigned (in whole or in part) to the assignee of the present patent application, and all of which patents are hereby incorporated herein by reference in their entirety.

While it will be apparent to one skilled in the art that the sensor technology has been the subject of considerable innovation and development from the aforementioned patents, how the data generated from the inspections performed using the sensors has been used and its availability to the operator of a glass container inspection machine has been considerably less developed. It will be appreciated that it may be beneficial to provide systems and methods to make such data relating to inspections of glass containers and particularly to any defects identified therein more readily available to the operator of the glass container inspection machine, as well as to make such data considerably more detailed in its nature.

The subject matter discussed in this background of the invention section should not be assumed to be prior art merely as a result of its mention in the background of the invention section. Similarly, a problem mentioned in the background of the invention section or associated with the subject matter of the background of the invention section should not be assumed to have been previously recognized in the prior art. The subject matter in the background of the invention section merely represents different approaches, which in and of themselves may also be inventions.

SUMMARY OF THE INVENTION

In a system embodiment, a system for inspecting glass containers passing through a glass container inspection machine includes: a plurality of sensors installed in the glass container inspection machine to inspect glass containers as they pass through the glass container inspection machine and to generate sensor signals indicative of a plurality of sensed parameters of the glass containers; at least one processor configured to process the sensor signals received from the plurality of sensors, compare processed sensor signals to predetermined parameters, identify processed sensor signals that vary from the predetermined parameters, and generate image signals that graphically depict glass containers associated with processed sensor signals that vary from the predetermined parameters together with defect information associated with the parameters of such glass containers that vary from the predetermined parameters; and at least one touchscreen monitor configured to display images based upon the image signals and the defect information provided by the at least one processor in a slidable main user interface display larger than a size that can be displayed at any given time on the at least one touchscreen monitor, wherein the at least one touchscreen monitor is configured to be controlled by a user using gestures to slide the slidable main user interface display to access the entirety of the slidable main user interface display; wherein the at least one touchscreen monitor and the at least one processor are arranged and configured to allow a user to control the touchscreen using gestures to access and display additional images of glass containers having at least one defect.

In another system embodiment, a system for inspecting glass containers passing through a glass container inspection machine includes: a plurality of sensors installed in the glass container inspection machine to inspect glass containers as they pass through the glass container inspection machine and to generate sensor signals indicative of a plurality of sensed parameters of the glass containers; at least one processor configured to process the sensor signals received from the plurality of sensors, compare processed sensor signals to predetermined parameters, identify processed sensor signals that vary from the predetermined parameters, and generate image signals that graphically depict glass containers associated with processed sensor signals that vary from the predetermined parameters together with defect information associated with the parameters of such glass containers that vary from the predetermined parameters; and a touchscreen monitor operatively connected to the at least one processor and configured to display images based upon the image signals and the defect information provided by the at least one processor in a slidable main user interface display larger than a size that can be displayed at any given time on the touchscreen monitor, wherein the at least one processor is configured to receive and interpret the gesture data and in response to provide image signals to the at least one touchscreen monitor, and wherein the touchscreen monitor is configured to be controlled by a user using gestures to slide the slidable main user interface display to access the entirety of the slidable main user interface display; wherein the touchscreen monitor and the at least one processor are arranged and configured to allow a user to control the touchscreen monitor using gestures to access and display additional images of glass containers having at least one defect; and wherein the at least one processor is configured to interact with the at least one touchscreen monitor such that when any of a plurality of discrete portions of the slidable main user interface display is displayed on the at least one touchscreen monitor and is accessed by a user gesture on the at least one touchscreen monitor, the at least one processor will operate the at least one touchscreen monitor to display one of a plurality of images each having content respectively associated with one of the plurality of discrete portions of the slidable main user interface display.

In still another system embodiment, a system for inspecting glass containers in a glass container inspection machine includes: at least one sensor installed in the glass container inspection machine which generates at least one sensor signal indicative of at least one sensed parameter of the glass containers; at least one processor configured to process the at least one sensor signal, compare the processed sensor signal to at least one predetermined parameter, identify any processed sensor signal that varies from the predetermined parameter, and generate an image signal that graphically depicts any glass containers associated with a processed sensor signal that varies from the predetermined parameter together with associated defect information; and a touchscreen monitor configured to display an image based upon the image signal and the defect information in a main user interface display larger than a size displayable on the touchscreen monitor, wherein the touchscreen monitor is configured to be controlled by a user using gestures to view the entirety of the main user interface display and to access and display additional images of glass containers having at least one defect.

In a method embodiment, a method for inspecting glass containers passing through a glass container inspection machine includes: generating sensor signals indicative of a plurality of sensed parameters of glass containers as they pass through the glass container inspection machine to be inspected with a plurality of sensors installed in the glass container inspection machine; processing the sensor signals received from the plurality of sensors with at least one processor; comparing processed sensor signals to predetermined parameters and identifying processed sensor signals that vary from the predetermined parameters; generating image signals that graphically depict glass containers associated with processed sensor signals that vary from the predetermined parameters together with defect information associated with the parameters of such glass containers that vary from the predetermined parameters; displaying images associated with the image signals and the defect information provided by the at least one processor on a touchscreen monitor in a slidable main user interface display larger than a size that can be displayed at any given time on the touchscreen monitor; controlling the touchscreen in response to a user using gestures to slide the slidable main user interface display to access the entirety of the slidable main user interface display; and controlling the touchscreen in response to a user using gestures to access and display additional images of at least one glass container defect having parameters that vary from the predetermined parameters.

DESCRIPTION OF THE DRAWINGS

These and other advantages of the present invention are best understood with reference to the drawings, in which:

FIG. 11B is an alternate embodiment of an inspection setup screenshot that is accessible on the touchscreen monitor from the slidable single view screen shown in FIG. 10B which may be used to setup parameters used to assess glass containers in the single view screen shown in FIG. 10B;

DETAILED DESCRIPTION OF AN EXEMPLARY EMBODIMENT

Figure 1:
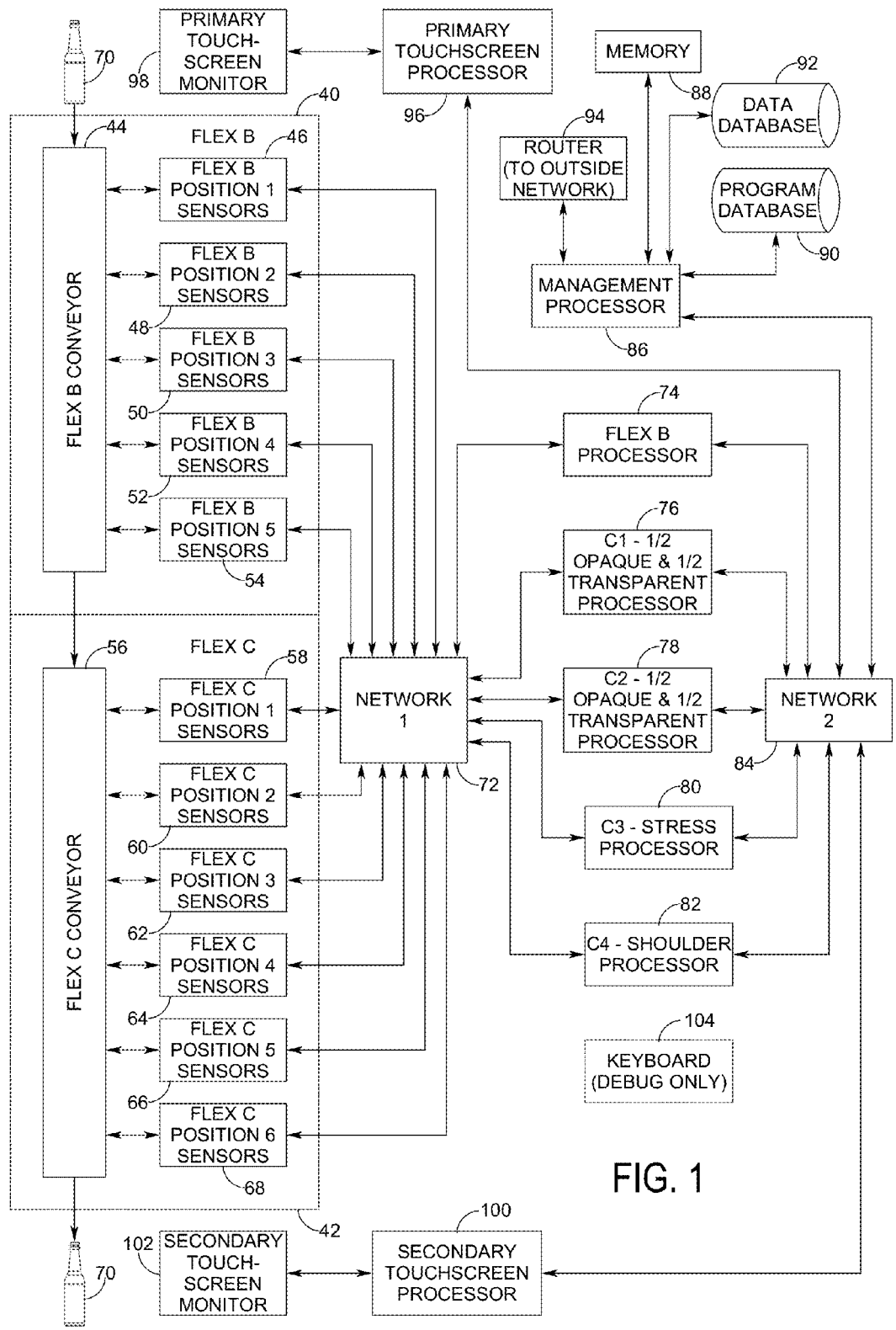
FIG. 1 is a somewhat schematic block diagram showing an overview of an exemplary system that may be used by the glass container inspection system and method having a graphic user interface of the present invention.

Prior to describing the glass container inspection system and method of the present invention, it is helpful to describe an exemplary glass container inspection machine that has been designed to implement the glass container inspection system and method the present invention with respect to FIG. 1. In a preferred embodiment, such a glass container inspection machine may include a Flex B inspection machine 40 and a Flex C inspection machine 42, which two units may together comprise a combined glass container inspection machine. (Alternately, either the Flex B inspection machine 40 or the Flex C inspection machine 42 may also be provided as independent stand-alone units.)

Glass containers enter the glass container inspection machine and proceed through a series of stations. At each station, different inspections are performed depending on the particular glass container inspection machine and its configuration. Each station uses a sensor of some sort to obtain useful information about the glass containers. Some sensors that may be used are cameras, pressure gauges, laser sensors, and light refraction detectors. Each glass container is then given a pass or fail for each inspection dependent on pre-established user criteria.

For some inspections, cameras may be used at various angles and locations with certain lighting to achieve a correct image for inspection. For example, for a sidewall inspection, six cameras may be positioned so they acquire full profile images from six distinct angles to ensure a full 360 degree image of the glass container. Another example is a dip inspection that uses a mechanical arm to place a rubber gasket on the top of a glass container, after which air is blown into the glass container. The amount of pressure built up in the glass container, or more precisely the lack thereof, can indicate a problem with the container. This rate of pressure may be displayed to a user through the machine interface, and be used in conjunction with controls to determine what constitutes a passing glass container.

The Flex B inspection machine 40 includes a Flex B conveyer 44 and five sensors or sensor sets located at five stations in the Flex B inspection machine 40. These sensors are Flex B position 1 sensors 46, Flex B position 2 sensors 48, Flex B position 3 sensors 50, Flex B position 4 sensors 52, and Flex B position 5 sensors 54. Similarly, the Flex C inspection machine 42 includes a Flex C conveyer 56 and six sensors or sensor sets located at six stations in the Flex C inspection machine 42. These sensors are Flex C position 1 sensors 56, Flex C position 2 sensors 58, Flex C position 3 sensors 60, Flex C position 4 sensors 62, Flex C position 5 sensors 64, and Flex C position 6 sensors 66.

In the preferred embodiment including the Flex B inspection machine 40 and the Flex C inspection machine 42, a stream of bottles 70 is supplied to the Flex B conveyer 44 in the Flex B inspection machine 40 and are conveyed past the five stations in the Flex B inspection machine 40. The bottles 70 then move from the Flex B conveyer 44 to the Flex C conveyer 56 in the Flex C inspection machine 42, and then the bottles 70 are conveyed past the six stations in the Flex C inspection machine 42. The bottles 70 then exit the inspection machine from the Flex C conveyer 56, after which rejected bottles 70 may be scrapped and good bottles 70 may be moved to finished goods.

By way of example, the Flex B inspection machine 40 may perform inspections such as inspections of the sealing surface, the base, base stress, vision plug gauging, wire edge, vision dip/saddle, and mold reading (wither bottom-up mold reading of top down alpha code/bottom dot reading). Similarly, by way of example, the Flex C inspection machine 42 may perform inspections such as opaque sidewall defect (six views) with dimensional inspection, transparent sidewall defect (six views), sidewall stress with polarized lighting (six views), and shoulder inspection (either opaque shoulder or stress shoulder). The Flex B inspection machine 40 and the Flex C inspection machine 42 are typically capable of inspecting round and non-round containers with heights from 38 mm to 381 mm and diameters from 16 mm to 170 mm, and can operate at speeds up to 600 glass containers per minute, depending upon container shape and size.

Also by way of example, descriptions of possible configurations of the sensors (none of which are shown in the drawings since all are known and understood by those skilled in the art) used in the Flex B inspection machine 40 and the Flex C inspection machine 42 will be briefly discussed. The Flex B position 1 sensors 46 may use a camera located directly above a bottle 70 with the focus of the camera being on the sealing surface of the bottle 70 for detection of defects such as line-over finish defects. The Flex B position 2 sensors 48 may use a single vision mold number reader ("MNR") camera located below a bottle 70 that is focused on the base of the bottle 70 from the outside.

The Flex B position 3 sensors 50 may use two cameras located above a bottle 70 in conjunction with mirrors located at a 45 degree angle with the cameras being zoomed for a field of view inside the bottle 70 and focused on the base of the bottle 70, with one of the cameras having a polarization filter in place for inspecting base stress. The Flex B position 4 sensors 52 may use a vision plug camera located directly above the mouth of a bottle 70 and focused inside the mouth of the bottle 70, and this same camera may also be used with a secondary light located above the bottle 70 to provide wire edge detection as well. The Flex B position 5 sensors 54 may be a vision dip camera that is located above a bottle 70, with four mirrors giving the camera 45 degree angled views of the mouth of the bottle 70 from 360 degrees around the container.

The Flex C position 1 sensors 56, the Flex C position 2 sensors 58, the Flex C position 3 sensors 60, the Flex C position 4 sensors 62, the Flex C position 5 sensors 64, and the Flex C position 6 sensors 66 in the Flex C inspection machine 42 each have three cameras that are respectively located in the six stations at locations spaced 60 degrees apart to provide a full 360 degree inspection of a bottle 70. Each station has one camera oriented at a downward angle to provide a view of the shoulder of the bottle 70, with the combination of the six 6 stations providing a full 360 degree inspection of the shoulder of the bottle 70.

The other two cameras at each of the six stations in the Flex C inspection machine 42 are used in conjunction with mirrors to extend focal length and provide a profile view of the entire bottle 70. One camera in this profile position may be used with a polarization filter to provide a stress inspection. The other camera does not have a filter, and may be used with different lighting patterns to provide dimensional and transparent inspections of the container.

The cameras used in the Flex B inspection machine 40 and the Flex C inspection machine 42 are preferably high resolution cameras (e.g., 1.4 megapixels) to provide improved defect detection capabilities. Programmable long life LED illumination provides repeated, accurate results, and stable, precise, and efficient handling of the bottles 70 is achieved. Further, maximum throughput is achieved with optimal spacing of the bottles 70 being minimal to allow for reduced linear conveying speeds with excellent stability of the bottles 70. It should be noted that other types of sensors could be used as well, including mechanical sensors and laser sensors.

Referring again to FIG. 1, it may be seen that the Flex B position 1 sensors 46, the Flex B position 2 sensors 48, the Flex B position 3 sensors 50, the Flex B position 4 sensors 52, and the Flex B position 5 sensors 54 in the Flex B inspection machine 40 and the Flex C position 1 sensors 56, the Flex C position 2 sensors 58, the Flex C position 3 sensors 60, the Flex C position 4 sensors 62, the Flex C position 5 sensors 64, and the Flex C position 6 sensors 66 in the Flex C inspection machine 42 are all networked in a first network 72. This first network connects the sensors of the Flex B inspection machine 40 and the Flex C inspection machine 42 to five processors which process information received from the sensors in order to detect any of a wide variety of defects in the bottles 70.

A Flex B processor 74 is used to process the information from the Flex B position 1 sensors 46, the Flex B position 2 sensors 48, the Flex B position 3 sensors 50, the Flex B position 4 sensors 52, and the Flex B position 5 sensors 54 in the Flex B inspection machine 40. First and second opaque and transparent information processors 76 and 78 are used to process opaque and transparent information obtained from the sensors in the Flex C inspection machine 42. A stress processor 80 is used to process stress-related information obtained from the sensors in the Flex C inspection machine 42. A shoulder processor 82 is used to shoulder-related information obtained from the sensors in the Flex C inspection machine 42.

The Flex B processor 74, the first opaque and transparent information processor 76, the second opaque and transparent information processor 78, the stress processor 80, and the shoulder processor 82 are connected to a second network 84. The overall operation of the system shown in FIG. 1 is coordinated by a management processor 86 which is connected to the second network 84. The management processor 86 is operatively connected to a memory 88, a program database 90 for storing programming instructions including instructions for interpreting gestures on a touchscreen monitor, and a data database 92 for storing information and statistics regarding the inspections of the bottles 70 performed by the glass container inspection machine. Additionally, the management processor 86 is connected to a router 94 that may be used to provide outside access to the system.

The management processor 86 is connected via the second network 84 to a primary touchscreen processor 96 that operates a primary touchscreen monitor 98, and optionally to a secondary touchscreen processor 100 that operates a secondary touchscreen monitor 102. The primary touchscreen monitor 98 (and the optional secondary touchscreen monitor 102) generate gesture data representative of gestures made by a user touching the at least one touchscreen monitor, and in response to the gesture data the management processor 86 provide image signals to the primary touchscreen monitor 98 (and the optional secondary touchscreen monitor 102). A graphic user interface provided by the glass container inspection system and method of the present invention uses the primary touchscreen monitor 98 (and optionally the secondary touchscreen monitor 102) to provide a tremendous amount of information relating to defects detected in the bottles 70 that may be viewed and manipulated by a user using the touchscreen monitor 98 (and optionally the secondary touchscreen monitor 102). In fact, the only need for a keyboard 104 is for debugging the glass container inspection system during installation or software updates.

The operation of the glass container inspection system and method having a graphic user interface is illustrated with regard to the images and screenshots of FIGS. 2-19. The user interface may be used to set up the glass container inspection machine parameters, as well as the details of the various inspections that are performed. The glass container inspection system and method having a graphic user interface of the present invention gives a user control over the glass container inspection machine to better enable a user to inspect, identify, and classify glass containers in a production line setting. The glass containers 70 are then handled appropriate depending on the results and preferences established by the user, with rejected containers being commonly diverted to another conveyor (not shown herein) and processed for recycling or disposal.

Figure 2:
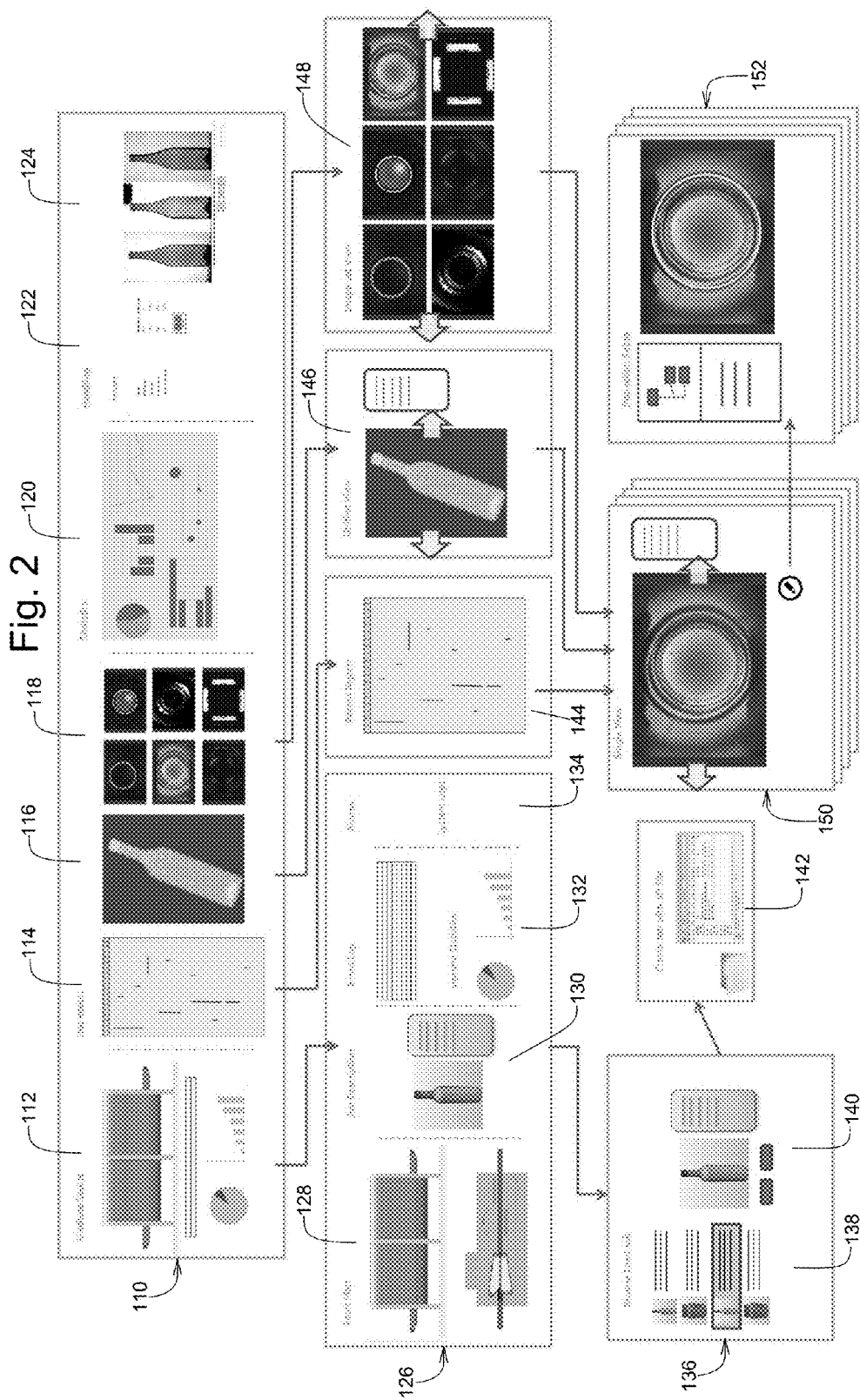
FIG. 2 is a schematic depiction of a slidable main user interface image that may be viewed on a touchscreen monitor and scrolled from side-to-side to view the entire user interface, as well as several other images and screenshots of images and information that can be accessed from the main user interface image.

Referring initially to FIG. 2, the main user interface image 110 displayed on the touchscreen monitor 98 (and optionally the secondary touchscreen monitor 102, both of which are shown in FIG. 1) from which a user can access information and review images of defects is shown as the top third of FIG. 2 (with the middle third and the bottom third including schematic depictions of other screens that can be accessed from the main user interface image 110). It will be understood that only a portion of the main user interface image 110 can be displayed on the touchscreen monitor 98 (and optionally the secondary touchscreen monitor 102, not shown in FIG. 1) at a time, but the user can use gestures (e.g., a fingertip sliding either rightward or leftward (or up and down) on the touch-sensitive face of the touchscreen monitor (and optionally the secondary touchscreen monitor 102)) to slide the main user interface image 110 from side-to-side (or move the image up or down) on the touchscreen monitor 98 (and optionally the secondary touchscreen monitor 102) to allow the user to view the entirety of the main user interface image 110.

Through the use of the main user interface image 110 as an information hub, high level information is available to the user with little interaction required by the user, thereby presenting relevant information to the user without overwhelming the user with details. In describing the operation of the glass container inspection system and method herein, it will be understood that when there is a reference to either viewing the primary touchscreen monitor 98 or using a gesture on the primary touchscreen monitor 98, the same image may optionally be viewed on the secondary touchscreen monitor 102 and the same gesture may optionally be used on the secondary touchscreen monitor 102.

It may be seen in FIG. 2 that the main user interface image 110 includes a number of discrete portions from left to right, including a machine status portion 112, an inspection portion 114, a unified view portion 116, an image set portion 118, a statistics portion 120, a handling portion 122, and a station offset portion 124. From a number of these portions on the main user interface image 110 (the machine status portion 112, the inspection portion 114, the unified view portion 116, and the image set portion 118), the user may use gestures (e.g., a tap or a double tap with a finger on the touch-sensitive face of the touchscreen monitor 98 (shown in FIG. 1)) to access another screen having additional images and/or additional information with content associated with the selected portion on the main user interface image 110.

For example, by the gesture of tapping on the machine status portion 112 of the main user interface image 110 on the primary touchscreen monitor (shown in FIG. 1), a machine status image 126 will be displayed on the touchscreen monitor 98 (shown in FIG. 1) from which a user can access machine status information displayed in images. The machine status image 126 is shown as the middle third of FIG. 2 at the left side thereof. Like the main user interface image 110, it will be understood that only a portion of the machine status image 126 can be displayed on the touchscreen monitor 98 at a time, but the user can use the gestures of a fingertip sliding either rightward or leftward on the touch-sensitive face of the touchscreen monitor 98 to slide the machine status image 126 from side-to-side on the touchscreen monitor to allow the user to view the entirety of the machine status image 126.

It may be seen in FIG. 2 that the machine status image 126 includes a number of discrete portions from left to right, including a fault map portion 128, a job description portion 130, an event log portion 132, and an alarm portion 134. From the job description portion 130 of the machine status image 126, the user may use a tap or double tap gesture on the touch-sensitive face of the touchscreen monitor 98 (shown in FIG. 1) to access a job description image 136 which will be displayed on the touchscreen monitor 98 (shown in FIG. 1), from which a user can access job description information displayed in an image. The job description information may include, for example, job list information 138 or current job description information 140, which will be described in more detail later in conjunction with FIG. 5. From the job list information 138 portion of the job description image 136, a load or create job image 142 may be accessed.

From the main user interface image 110, the user may use a tap or double tap gesture on the inspection portion 114 of the main user interface image 110 on the touch-sensitive face of the touchscreen monitor 98 (shown in FIG. 2) to access a recent results image 144 which will be displayed on the touchscreen monitor 98 (shown in FIG. 1) to view job description information, which will be described in more detail later in conjunction with FIG. 7.

From the main user interface image 110, the user may use a tap or double tap gesture on the unified view portion 116 of the main user interface image 110 on the touch-sensitive face of the touchscreen monitor 98 (shown in FIG. 1) to access a unified view image 146 which will be displayed on the touchscreen monitor 98 (shown in FIG. 1) to view job description information. The unified view image 146 will be described in more detail later in conjunction with FIG. 8.

From the main user interface image 110, the user may use a tap or double tap gesture on the image set portion 118 of the main user interface image 110 on the touch-sensitive face of the touchscreen monitor (shown in FIG. 1) to access an image set image 148 which will be displayed on the touchscreen monitor 98 to view image sets of the bottles 70. The image set image 148 will be described in more detail later in conjunction with FIGS. 9A, 9B, and 9C.

From any of the recent results image 144, the unified view image 146, or the image set image 148, the user may use a tap or double tap gesture on the touch-sensitive face of the touchscreen monitor 98 (shown in FIG. 1) to access a single view image 150. The single view image 150 will allow the user to access and view all of the images associated with a bottle 70 that has been rejected by the use of gestures on the touch-sensitive face of the touchscreen monitor 98 (shown in FIG. 1). Additionally, from the single view image 150, the user can access inspection setup screens to set rejection parameters for all of the different inspections made by the glass container inspection machine. The single view image 150 will be described in more detail later in conjunction with FIGS. 10A and 10B.

From the single view image 150, the user may use a gesture on the touch-sensitive face of the touchscreen monitor 98 (shown in FIG. 1) to access an inspection setup image 152. The inspection setup process allows the user to control sensor settings as well as allowing the user to define tolerances for the various inspections to be performed. The inspection setup image 152 will be described in more detail later in conjunction with FIGS. 11A and 11B.

Figure 3:
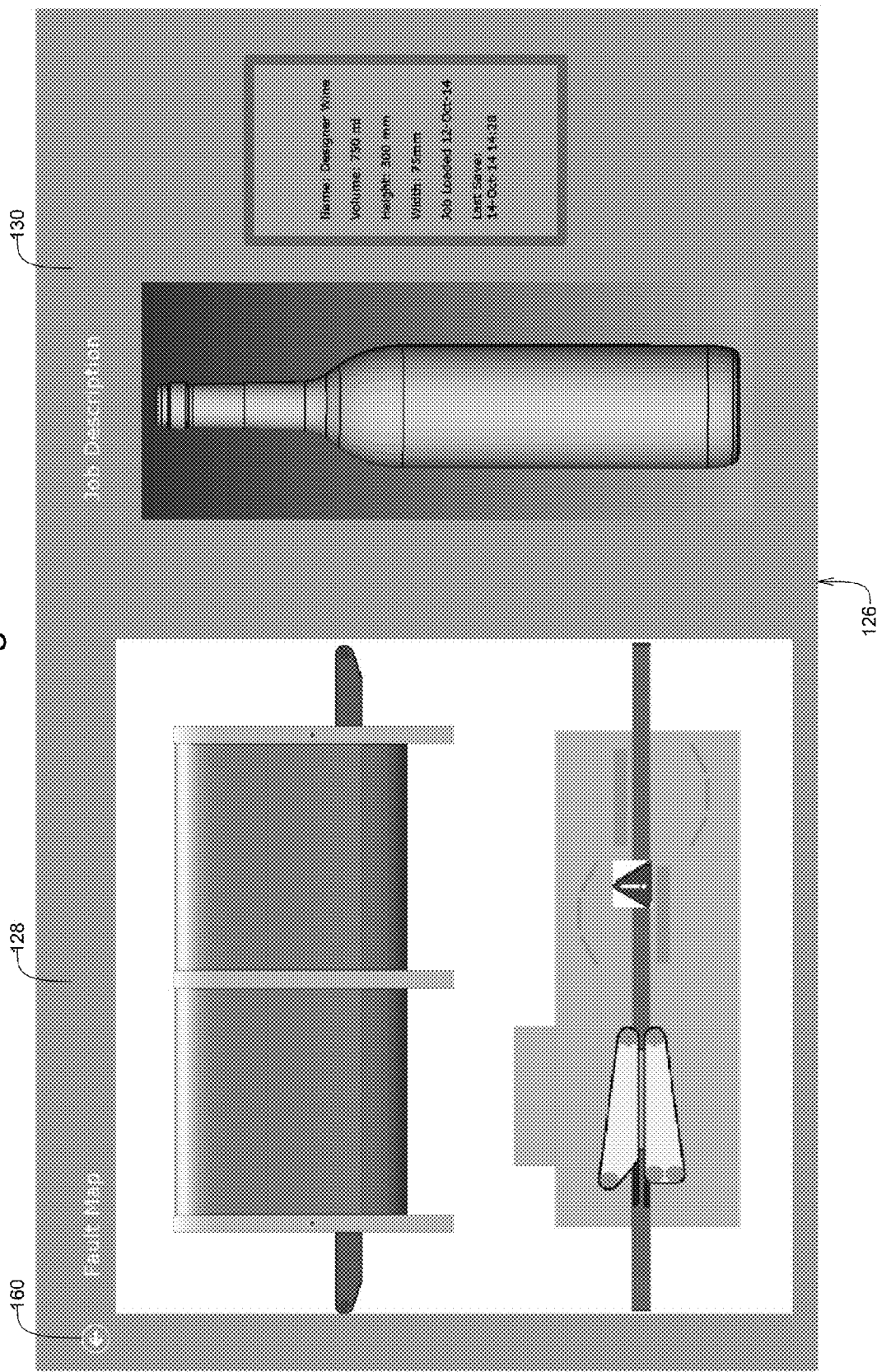
FIG. 3 is the leftmost portion of a slidable machine status information screenshot that is accessible on the touchscreen monitor from the main user interface screen shown in FIG. 2 which shows information relating to a fault map depicting the operational status of a glass container inspection machine and a job description providing information relating to the current job being performed by the glass container inspection machine.
Figure 4:
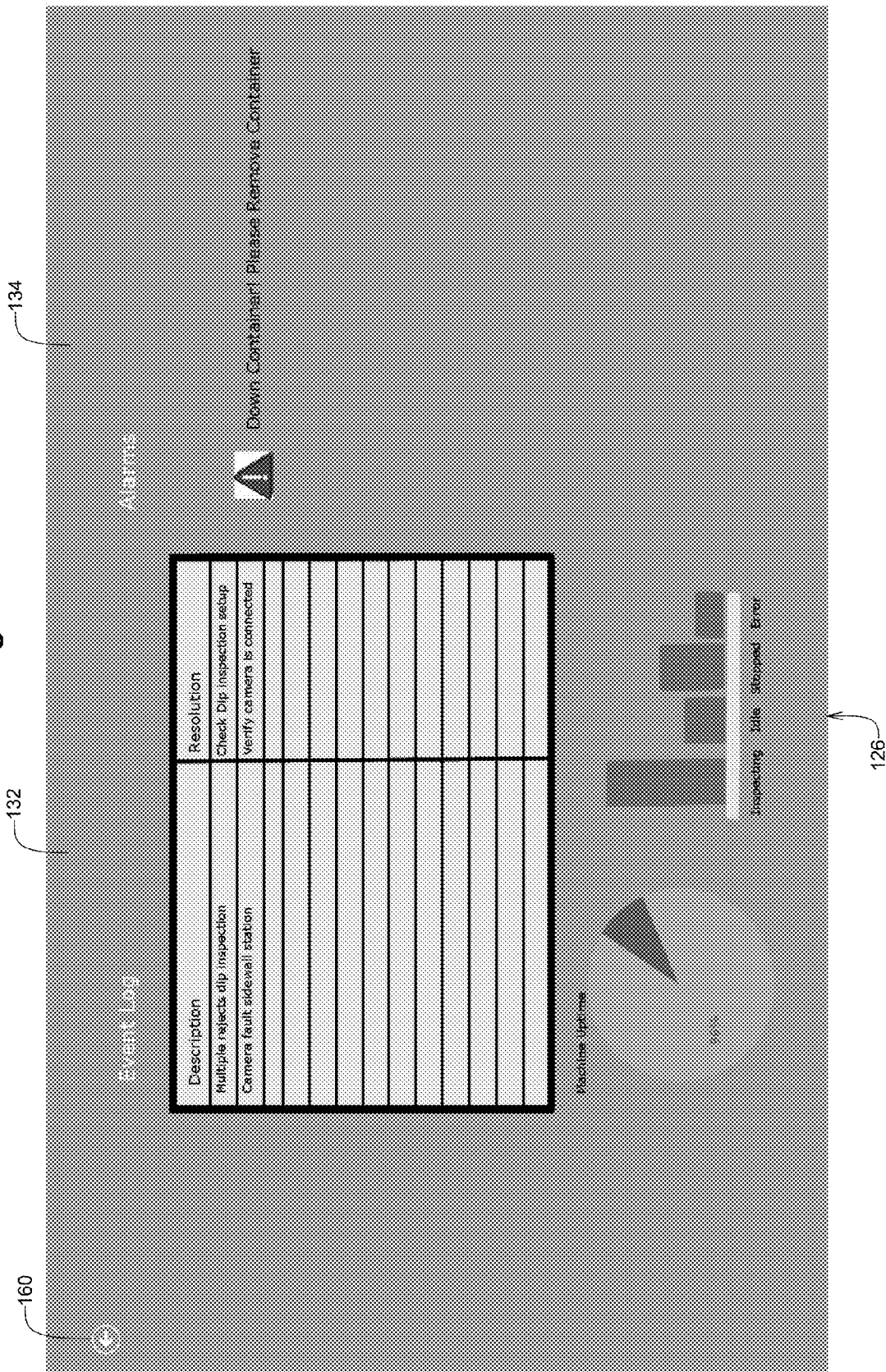
FIG. 4 is the rightmost portion of the slidable machine status information screenshot accessible on the touchscreen monitor from the main user interface screen shown in FIG. 2 which shows event log information relating to events, uptime statistics relating to performance statistics, and alarms that have occurred, all relating to the operation of the glass container inspection machine.

Referring next to FIGS. 3 and 4, the machine status image 126 accessed from the machine status portion 112 of the main user interface image 110 (Shown in FIG. 2) is illustrated. The machine status image 126 provides a graphical representation of the machine in the fault map portion 128, a description of the particular glass container 70 being evaluated in the job description portion 130, a brief event log and utilization information such as uptime in the event log portion 132, and any information related to an alarm event in the alarm portion 134.

The functionality of the machine status image 126 is to give the user a single screen to determine if the glass container inspection machine is in a functional state, as well as to provide directions to get the glass container inspection machine running again if it is currently non-functional. It will be appreciated that the machine status image 126 shown in FIGS. 3 and 4 is too wide for it to be displayed on the touchscreen monitor 98 (shown in FIG. 1) in its entirety, but the user can use the gestures of a fingertip sliding either rightward or leftward on the touch-sensitive face of the touchscreen monitor 98 to slide the machine status image 126 from side-to-side on the touchscreen monitor 98 to allow the user to view the entirety of the machine status image 126. In order to return to the main user interface image 110 (shown in FIG. 2) from the machine status image 126 shown in FIGS. 3 and 4, the user can use a tapping gesture on a return to main screen button 160, which will return the image displayed on the primary touchscreen monitor 98 to the main user interface image 110.

Figure 5:
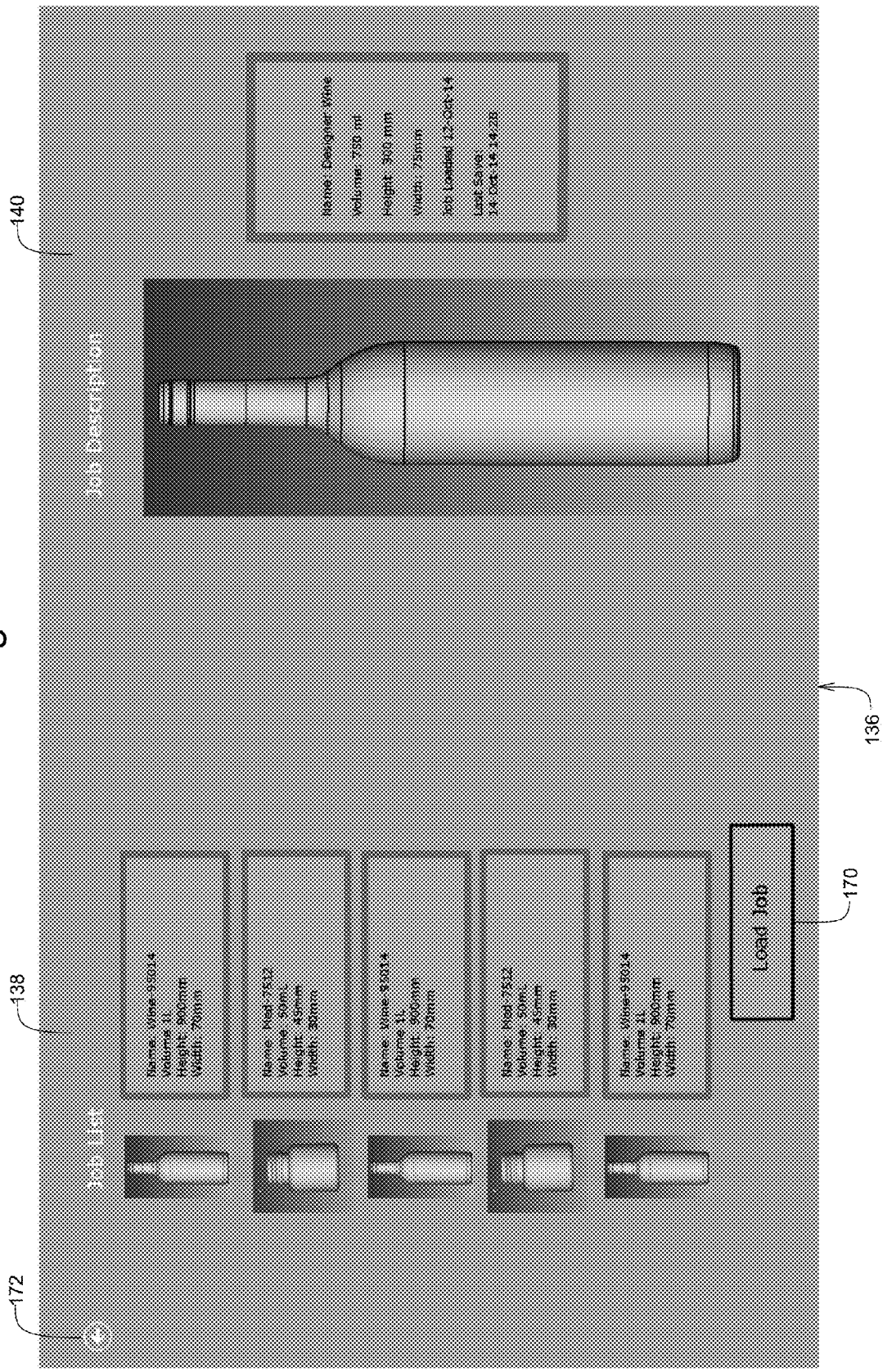
FIG. 5 is a browse load job screenshot accessible on the touchscreen monitor from the slidable machine status information screen shown in FIG. 3 which shows the most recent jobs performed by the glass container inspection machine as well as information relating to the current job being performed by the glass container inspection machine.

Referring now to FIG. 5, the job description image 136 accessed from the machine status portion 112 of the main user interface image 110 (Shown in FIG. 2), which provides detailed fault information and system status information, is illustrated. The job description image 136 provides a graphical representation of the machine in the fault map portion 128 (which depicts any faults and a graphic depiction of the location of the fault in the glass container inspection machine), a description of what kind of glass container 70 is being inspected and evaluated in the job description portion 130, a brief event log with details on the glass container inspection machine's health statistics and events and utilization information such as uptime in the event log portion 132 (which also displays a log of information for historical purposes), and any information related to an alarm event in the alarm portion 134.

Figure 6:
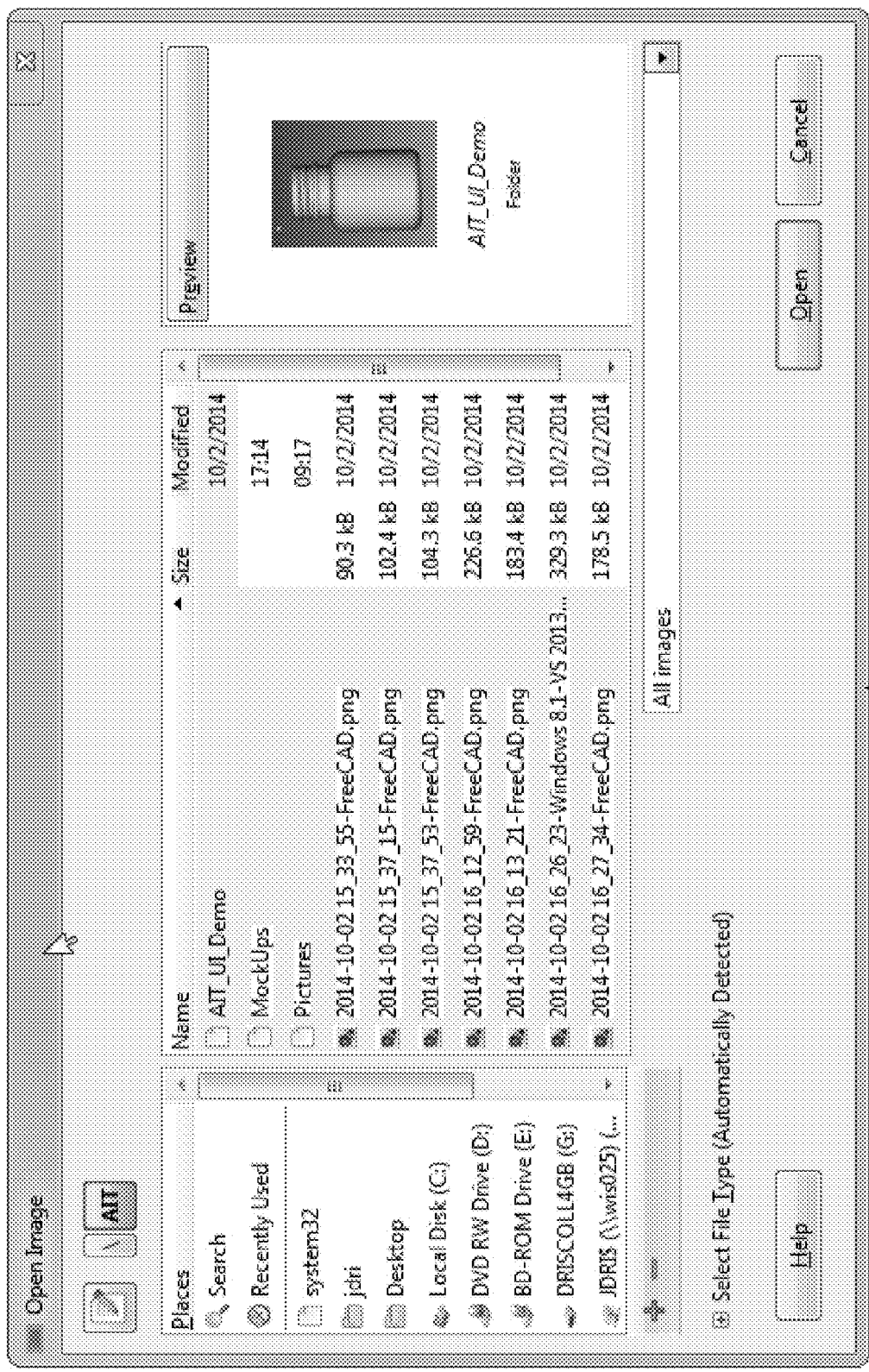
FIG. 6 is create job screenshot accessible on the touchscreen monitor from the browse load job screen shown in FIG. 5 to select a new job for the glass container inspection machine to perform.

The job description image 136 provides the user even more detailed information about a job along with the availability of a job library by selecting a load job button 170 on the job description image 136 with a tapping gesture on the load job button 170, which causes the load or create job image 142 best shown in FIG. 6 to be displayed on the primary touchscreen monitor 98 (shown in FIG. 1). From the load or create job image 142 the user can load or create new jobs. As a further extension, the user can import a 3D file such as a *.stl file for a new job. From doing so the job will gather useful information about the glass container and provide some initial setup information for the user, along with the corresponding inspections. In order to return to the main user interface image 110 (shown in FIG. 2) from the job description image 136 shown in FIG. 5, the user can use a tapping gesture on a return to main screen button 172, which will return the image displayed on the primary touchscreen monitor 98 to the main user interface image 110.

Figure 7:
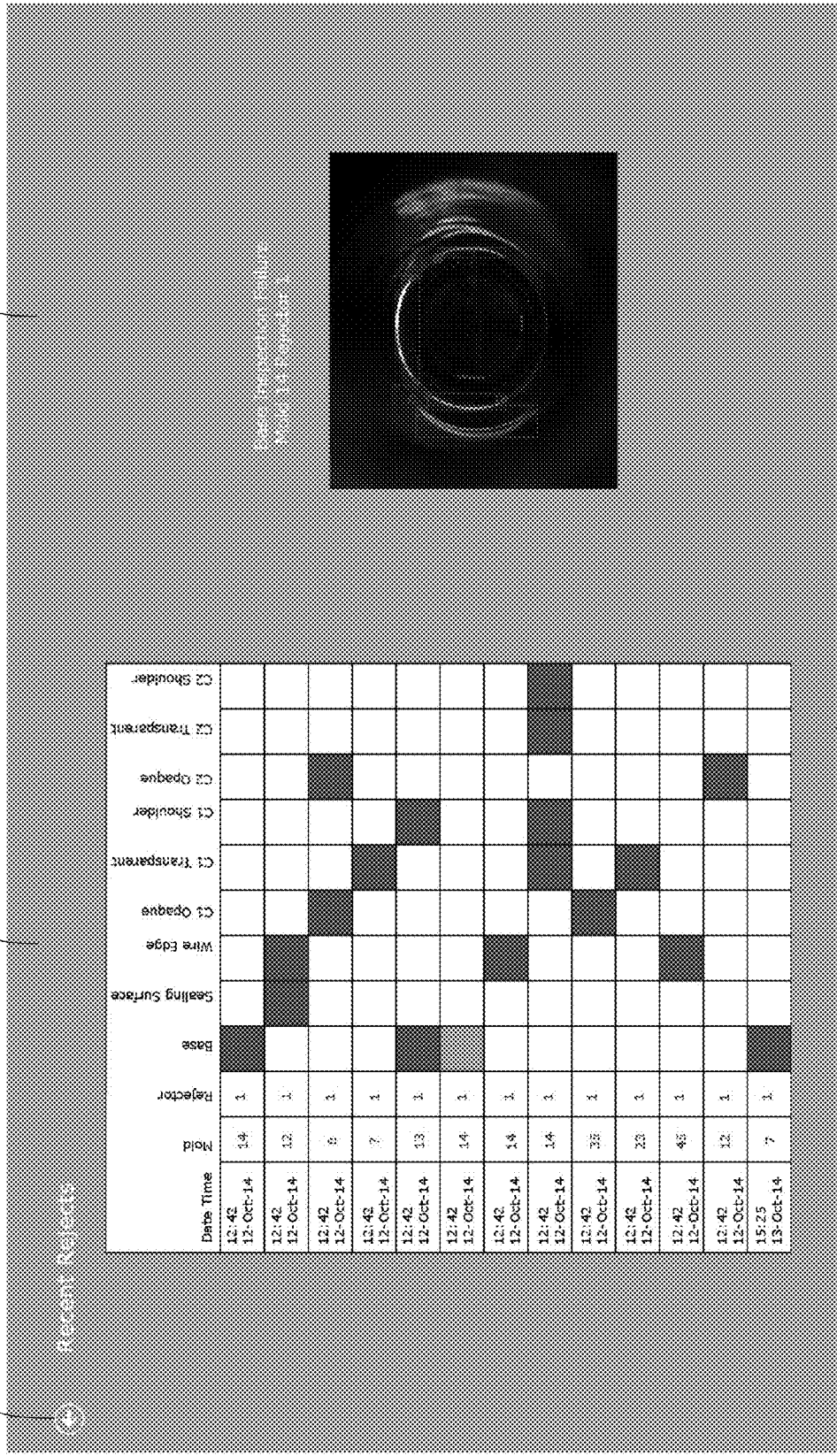
FIG. 7 is a recent rejects information screenshot that is accessible on the touchscreen monitor from the main user interface screen shown in FIG. 2 which shows information relating to a glass container that has been rejected recently by the glass container inspection machine as well as an image of a rejected glass container showing a detected defect.

Referring next to FIG. 7, the recent results image 144 accessed from the inspection portion 114 of the main user interface image 110 (shown in FIG. 2), which provides a detailed grid view 180 of recently rejected bottles 70, is illustrated. Within the grid are indicators for why a bottle 70 was rejected that provide navigation to the failing sensor results, and inspection setup. Container information such as the time, the ID, and the resulting rejector are also displayed in the recent results image 144.

On the right of the recent results image 144, a single view 182 of a bottle 70 from the grid view 180 is shown that may be selected by a user using a tapping gesture on the desired line of the grid view 180 to display the image demonstrating why the particular bottle 70 was rejected. In order to return to the main user interface image 110 (shown in FIG. 2) from the recent results image 144 shown in FIG. 7, the user can use a tapping gesture on a return to main screen button 184, which will return the image displayed on the primary touchscreen monitor 98 (shown in FIG. 1) to the main user interface image 110.

Figure 8:
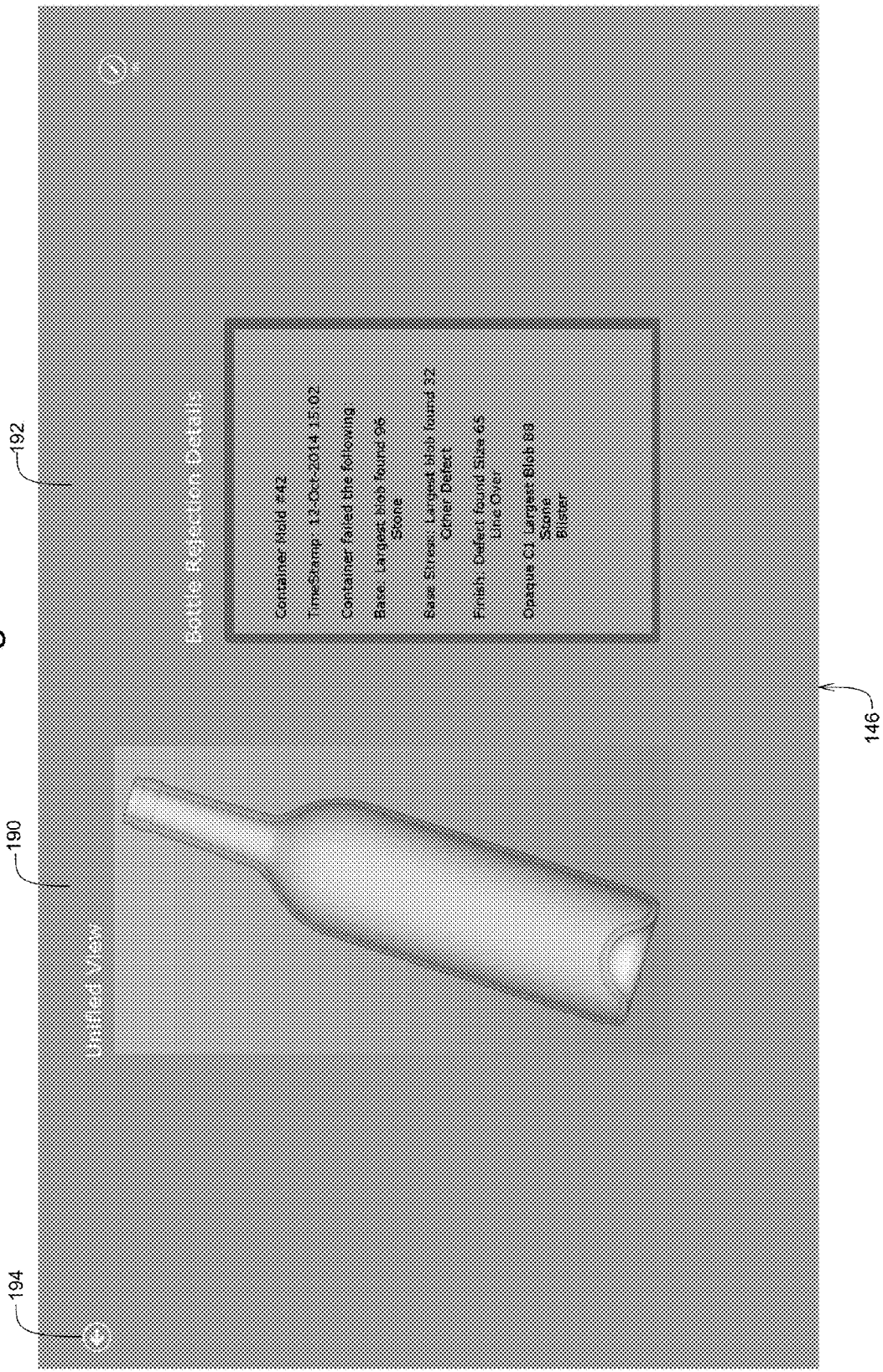
FIG. 8 is a unified view information screenshot that is accessible on the touchscreen monitor from the main user interface screen shown in FIG. 2 which shows information relating to a single container that has been rejected by the glass container inspection machine, including a three dimensional view of the rejected glass container as well as details relating to the rejected glass container.

Referring now to FIG. 8, the unified view image 146 accessed from the unified view portion 116 of the main user interface image 110 (shown in FIG. 2), which provides a unified view 190 of a recently rejected bottle 70 and some recent inspection results 192, is illustrated. In the unified view 190, the user can use gestures on the primary touchscreen monitor 98 (shown in FIG. 1) to move the rejected container displayed around to view it from any angle, and also pinch-to-zoom gestures to zoom in or out from the image shown. (For details of a pinch-to-zoom application see U.S. Pat. No. 7,844,915, to Platzer et al., and U.S. Patent Application Publication No. 2014/0298414, to Alsina et al., which are both hereby incorporated herein by reference.) As such, this view may be seen as a brief overview of the subsections of the inspection done on the bottle 70, and it is mainly a navigational point for getting to inspection sections. Details of the data on the rejected bottle 70 is provided in the recent inspection results 192.

The goal of the unified view image 146 is to provide the user with a comprehensive view of a bottle that has been rejected and the reasons for the rejection. The unified view 190 imported by the user is a 3D model that is associated with upwards of 30 inspection images and results attached to the interactive container in the appropriate locations. From here the user will be able to select different details from the unified view 190 that allows the user to view individual inspections and perform the required task of recording or modifying inspection setups. In order to return to the main user interface image 110 (shown in FIG. 2) from the unified view image 146 shown in FIG. 8, the user can use a tapping gesture on a return to main screen button 194, which will return the image displayed on the primary touchscreen monitor 98 (shown in FIG. 1) to the main user interface image 110.

Figure 9A:
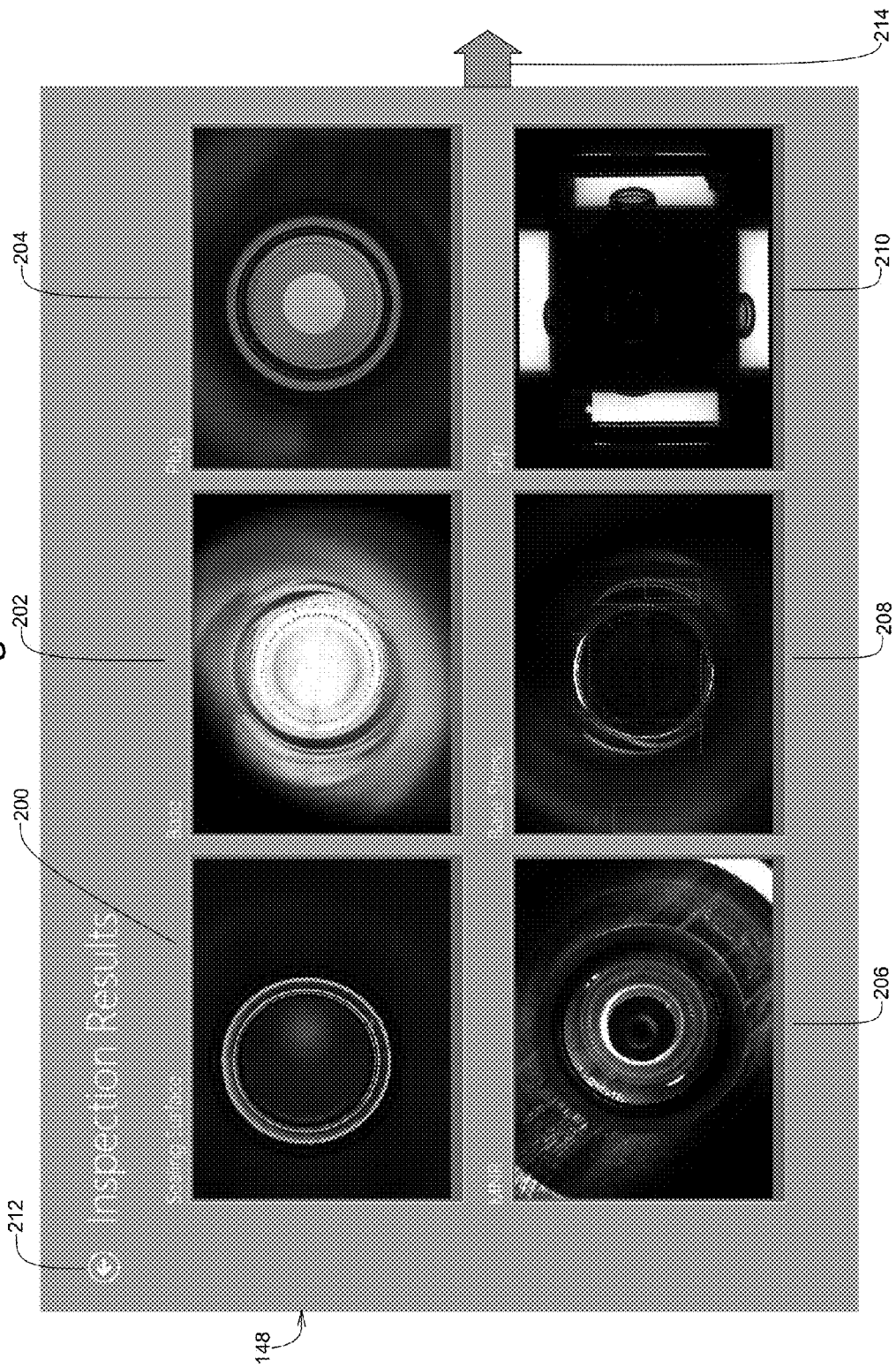
FIG. 9A-9C are respectively the leftmost portion, the central portion, and the rightmost portion of a slidable inspection results screenshot that is accessible on the touchscreen monitor from the main user interface screen shown in FIG. 2 which show all of the images relating to a rejected glass container.
Figure 9B:
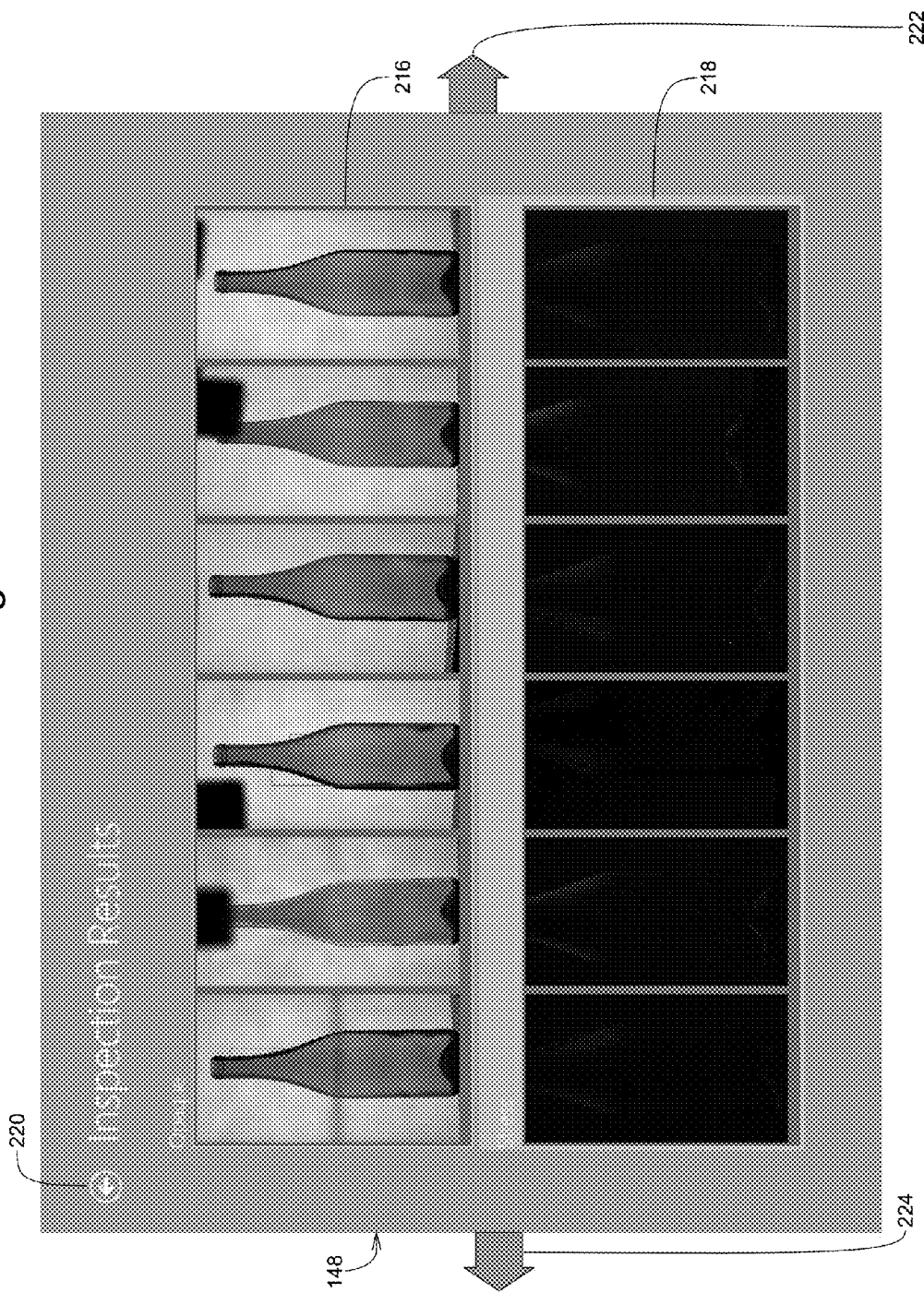
Figure 9C:
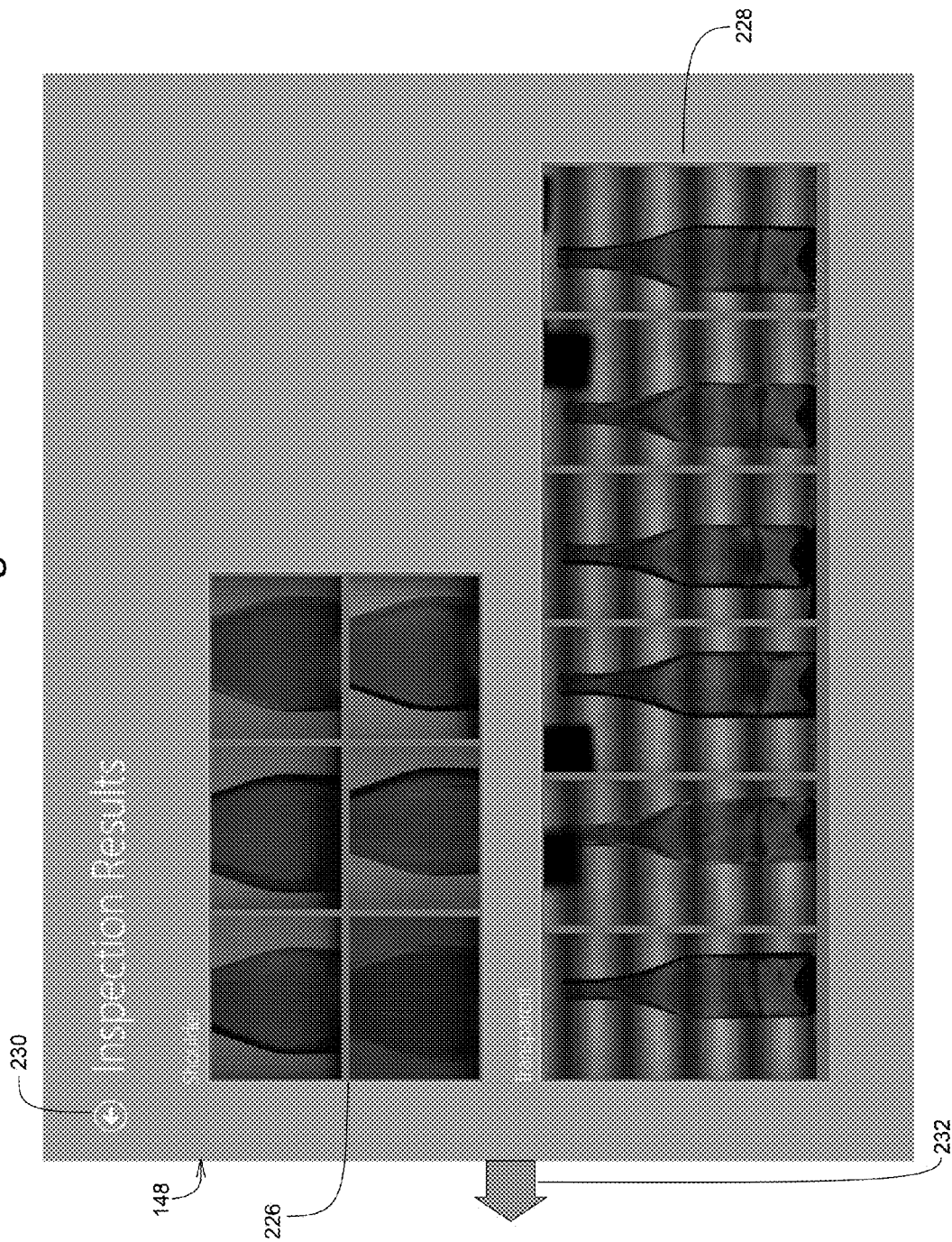

Referring next to FIGS. 9A, 9B, and 9C, the image set image 148 accessed from the image set portion 118 of the main user interface image 110 (shown in FIG. 2), which provides a complete set of all of the images of a recently rejected bottle 70 is illustrated. It will be understood that only a portion of the image set image 148 can be displayed on the touchscreen monitor 98 (shown in FIG. 1) at a time, but the user can use the gestures of a fingertip sliding either rightward or leftward on the touch-sensitive face of the touchscreen monitor 98 to slide the image set image 148 from side-to-side on the touchscreen monitor 98 to allow the user to view all of the images of a recently rejected bottle 70.

Referring first to FIG. 9A, the views of the rejected bottle 70 that are illustrated are a sealing surface image 200, a base image 202, a plug image 204, a mold number reader image 206, a base stress image 208, and a dip image 210. In order to return to the main user interface image 110 (shown in FIG. 2) from the image set image 148 shown in FIG. 9A, the user can use a tapping gesture on a return to main screen button 212, which will return the image displayed on the primary touchscreen monitor 98 (shown in FIG. 1) to the main user interface image 110. By a user using a tapping gesture on a next-screen-to-the-right button 214, the view on the primary touchscreen monitor 98 (shown in FIG. 1) will move from the view shown in FIG. 9A to the view shown in FIG. 9B.

Referring next to FIG. 9B, the views of the rejected bottle 70 that are illustrated are six opaque images 216 (all taken at angles 60 degrees displaced from each other) and six stress images 218 (all taken at angles 60 degrees displaced from each other). In order to return to the main user interface image 110 (shown in FIG. 2) from the image set image 148 shown in FIG. 9B, the user can use a tapping gesture on a return to main screen button 220, which will return the image displayed on the primary touchscreen monitor 98 (shown in FIG. 1) to the main user interface image 110. By a user using a tapping gesture on a next-screen-to-the-right button 222, the view on the primary touchscreen monitor 98 (shown in FIG. 1) will move from the view shown in FIG. 9B to the view shown in FIG. 9C. Also, by a user using a tapping gesture on a next-screen-to-the-left button 224, the view on the primary touchscreen monitor 98 (shown in FIG. 1) will move from the view shown in FIG. 9B to the view shown in FIG. 9A.

Referring now to FIG. 9C, the views of the rejected bottle 70 that are illustrated are six shoulder images 226 (all taken at angles 60 degrees displaced from each other) and six transparent images 228 (all taken at angles 60 degrees displaced from each other). In order to return to the main user interface image 110 (shown in FIG. 2) from the image set image 148 shown in FIG. 9C, the user can use a tapping gesture on a return to main screen button 230, which will return the image displayed on the primary touchscreen monitor 98 (shown in FIG. 1) to the main user interface image 110. By a user using a tapping gesture on a next-screen-to-the-left button 232, the view on the primary touchscreen monitor 98 (shown in FIG. 1) will move from the view shown in FIG. 9C to the view shown in FIG. 9B.

Figure 10A:
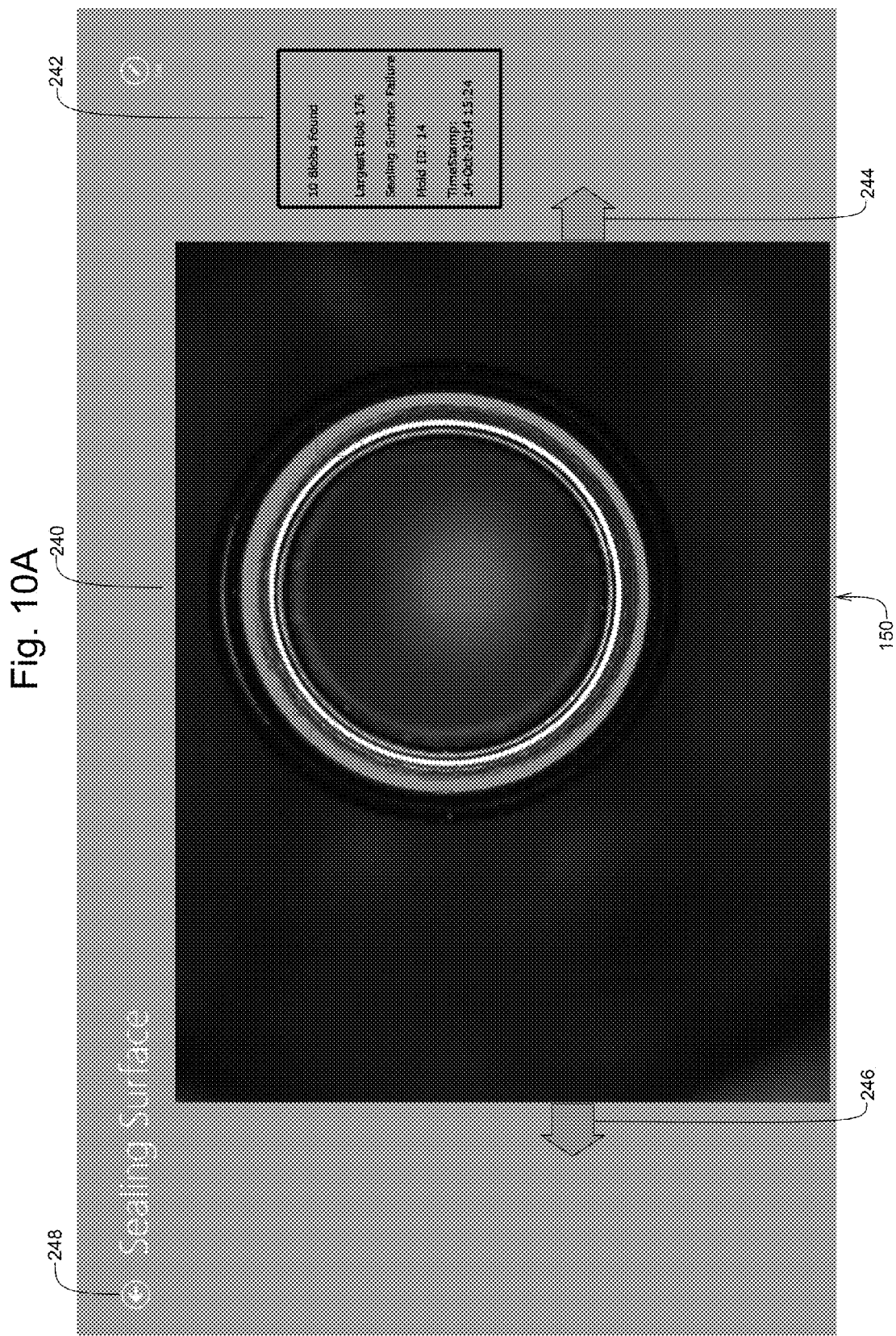
FIG. 10A is a preferred embodiment of a slidable single view screenshot that is accessible on the touchscreen monitor from the recent rejects information screen shown in FIG. 7, the unified view information screen of FIG. 8, or the inspection results screen of FIG. 9 which may be used to review each of the various images of a rejected glass container.

Referring now to FIG. 10A, an inspection single view image 240 (that is one of at least 30 different images available for a rejected bottle 70) and related sensor results 242 for the rejected bottle 70 are shown in the single view image 150. The primary purpose of the inspection single view image 240 is to provide navigation to the different inspection details of the images and sensor results from the various sensors in the inspection stations on the glass container inspection machine. By using pinch-to-zoom gestures on the primary touchscreen monitor 98 (shown in FIG. 1) to zoom in or out from the image shown in the inspection single view image 240, and sliding gestures on the primary touchscreen monitor 98 to move the image up and down and back and forth, a user can zoom in and out to view enlarged portions of the inspection single view image 240.

By a user using a tapping gesture on a next-image-to-the-right button 244, the view on the primary touchscreen monitor 98 (shown in FIG. 1) will move from the image shown in FIG. 10A to the next image. Similarly, by a user using a tapping gesture on a next-image-to-the-left button 246, the view on the primary touchscreen monitor 98 will move from the image shown in FIG. 10A to the previous image. In this way, all of the images of a rejected bottle 70 can be viewed and manipulated in a similar manner. In order to return to the main user interface image 110 (shown in FIG. 2) from the single view image 150 shown in FIG. 10A, the user can use a tapping gesture on a return to main screen button 248, which will return the image displayed on the primary touchscreen monitor (shown in FIG. 1) to the main user interface image 110.

Referring now to FIG. 10A', an alternate embodiment inspection single view image 240' (that is one of at least 30 different images available for a rejected bottle 70) and related sensor results 242' for the rejected bottle 70 is shown in the single view image 150. The primary purpose of the inspection single view image 240' is to provide navigation to the different inspection details of the images and sensor results from the various sensors in the inspection stations on the glass container inspection machine. By using pinch-to-zoom gestures on the primary touchscreen monitor 98 (shown in FIG. 1) to zoom in or out from the image shown in the inspection single view image 240', and sliding gestures on the primary touchscreen monitor 98 to move the image up and down and back and forth, a user can zoom in and out to view enlarged portions of the inspection single view image 240'. It will be noted that the inspection single view image 240' is provided with boxes that highlight defects in the image of the rejected bottle 70.

By a user using a tapping gesture on a next-image-to-the-right button 244', the view on the primary touchscreen monitor 98 (shown in FIG. 1) will move from the image shown in FIG. 10A' to the next image. Similarly, by a user using a tapping gesture on a next-image-to-the-left button 246', the view on the primary touchscreen monitor 98 will move from the image shown in FIG. 10A' to the previous image. In this way, all of the images of a rejected bottle 70 can be viewed and manipulated in a similar manner. In order to return to the main user interface image 110 (shown in FIG. 2) from the single view image 150 shown in FIG. 10A', the user can use a tapping gesture on a return to main screen button 248', which will return the image displayed on the primary touchscreen monitor (shown in FIG. 1) to the main user interface image 110.

Figure 11A:
FIG. 11A is a preferred embodiment of an inspection setup screenshot that is accessible on the touchscreen monitor from the slidable single view screen shown in FIG. 10A which may be used to setup parameters used to assess glass containers in the single view screen shown in FIG. 10A.

Referring now to FIG. 11A, an inspection setup single view image 250 (that corresponds to one of the least 30 different the inspection single view images 240 available for a rejected bottle 70 in FIG. 10A) and related parameter settings 252 (that correspond to the sensor results 242 related to the corresponding inspection single view images 240) are shown in the inspection setup image 152. This is the image from which a user may set up each of the different inspections. There is a section for the sensor information, or image from a camera, and there is a separate area in which to provide the various tools used for inspection. Upon selection of a specific tool, the settings, or parameters, for that tool will be displayed to the user with the corresponding controls for manipulation by gestures on the primary touchscreen monitor 98 (shown in FIG. 1). This page is generated dynamically based on what kind of inspection is being performed and what tools are loaded and available to the user.

In similar fashion, the parameters for all of the images of a rejected bottle 70 can be viewed and manipulated in a similar manner. In order to return to the single view image 150 (shown in FIG. 10A) from the inspection setup image 152 shown in FIG. 11A, the user can use a tapping gesture on a return to single view image button 254, which will return the image displayed on the primary touchscreen monitor 98 (shown in FIG. 1) to the single view image 150.

Figure 10B:
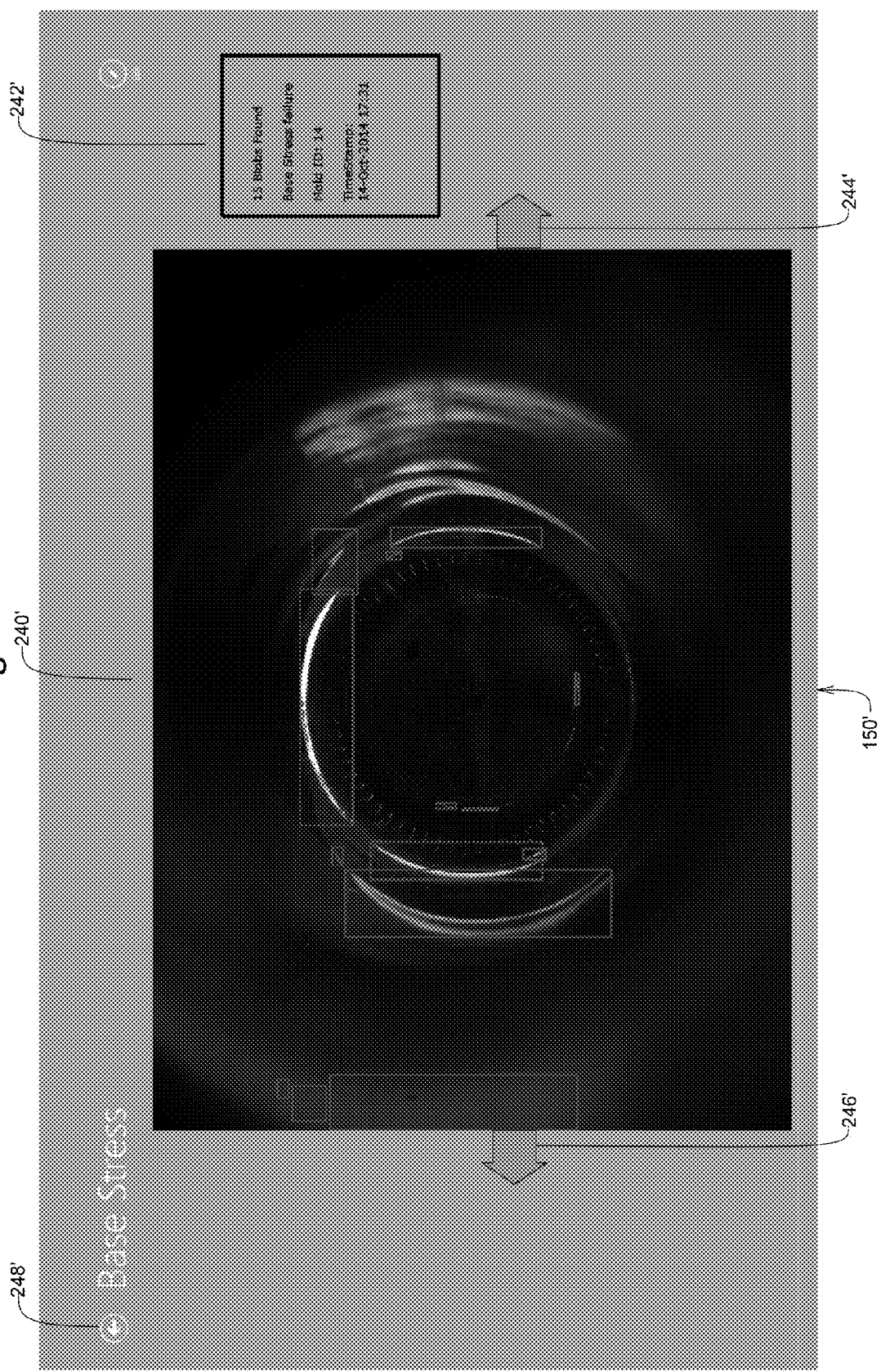
FIG. 10B is an alternate embodiment of a slidable single view screenshot that is accessible on the touchscreen monitor from the recent rejects information screen shown in FIG. 7, the unified view information screen of FIG. 8, or the inspection results screen of FIG. 9 which may be used to review each of the various images of a rejected glass container.

Referring next to FIG. 11B, an alternate embodiment inspection setup single view image 250' (that corresponds to one of at the least 30 different inspection single view images 240' available for a rejected bottle 70 in FIG. 10B) and related parameter settings 252' (that correspond to the sensor results 242' related to the corresponding inspection single view images 240') are shown in the inspection setup image 152'. This is the image from which a user may select from alternative highlights to show the original image, an image with defects highlighted, a zone image, or a defect image using gestures on the primary touchscreen monitor 98 (shown in FIG. 1). In order to return to the single view image 150' (shown in FIG. 10B) from the inspection setup image 152' shown in FIG. 11B, the user can use a tapping gesture on a return to single view image button 254', which will return the image displayed on the primary touchscreen monitor 98 to the single view image 150'.

Figure 12:
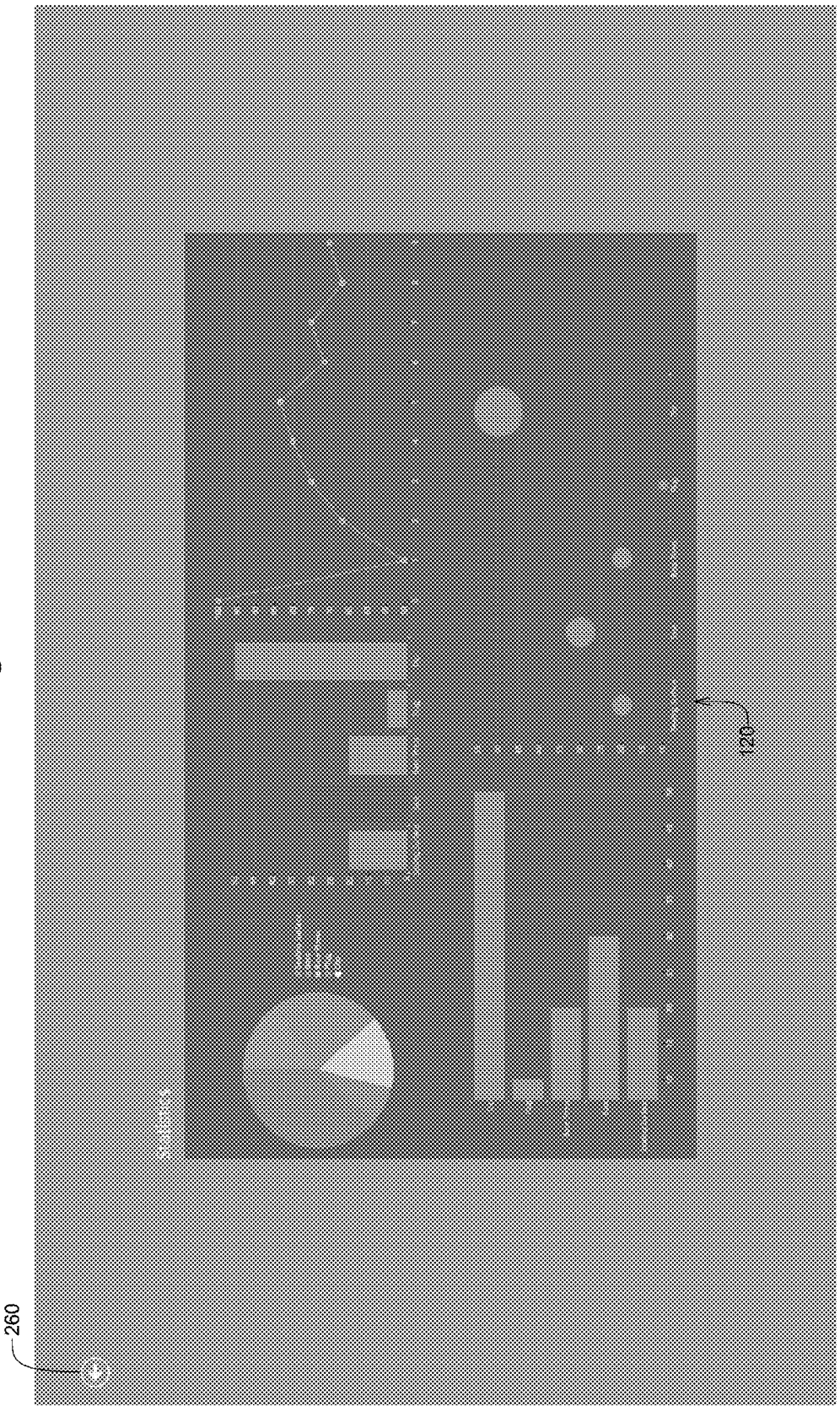
FIG. 12 is an enlarged portion of the slidable main user interface screen shown in FIG. 2 which shows information relating to statistics compiled by the glass container inspection machine.

Referring now to FIG. 12, an enlarged view of the statistics portion 120 of the main user interface image 110 (shown in FIG. 2) which may be accessed by a user by using a tap or double tap gesture on the statistics portion 120 of the main user interface image 110 on the touch-sensitive face of the touchscreen monitor 98 (shown in FIG. 1) is illustrated. Overall glass container inspection machine statistics are displayed here, such as total bottles 70 inspected, total bottles 70 rejected, and the reasons that the bottles 70 were rejected. Optionally from here, the user can navigate to an inspection section that displays more details. In order to return to the main user interface image 110 from the enlarged statistics portion 120 shown in FIG. 12, the user can use a tapping gesture on a return to main screen button 260, which will return the image displayed on the primary touchscreen monitor 98 to the main user interface image 110.

Figure 13:
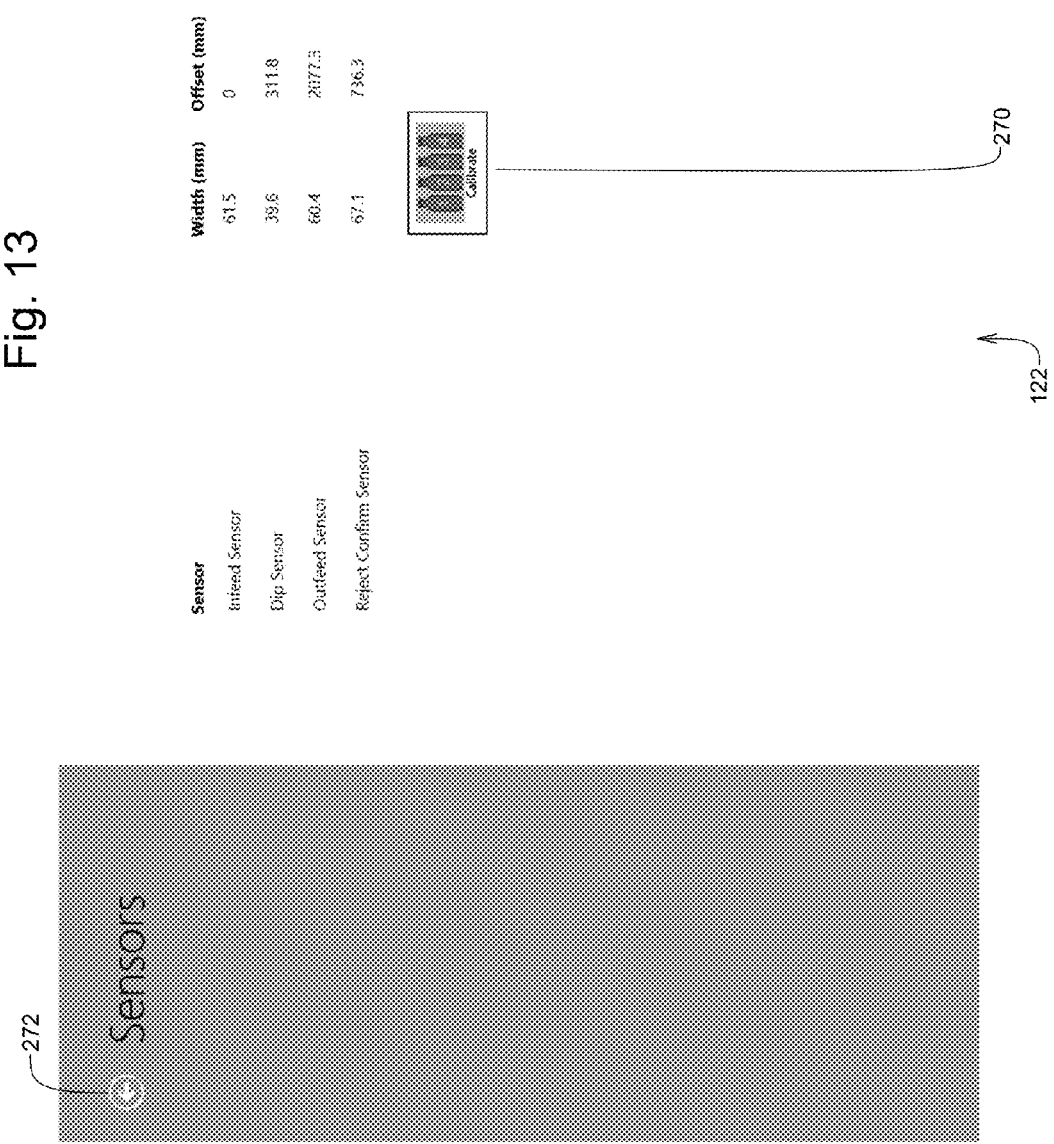
FIG. 13 is an enlarged portion of the slidable main user interface screen shown in FIG. 2 which shows information relating to several sensors used by the glass container inspection machine.

Referring next to FIG. 13, an enlarged view of the sensor information portion 122 of the main user interface image 110 (shown in FIG. 2) which may be accessed by a user by using a tap or double tap gesture on the sensor information portion 122 of the main user interface image 110 on the touch-sensitive face of the touchscreen monitor 98 (shown in FIG. 1) is illustrated. Overall a number of sensor parameters are displayed here, such as the infeed sensor, the dip sensor, the outfeed sensor, and the reject confirm sensor.

The sensor information portion 122 provides an overview of the mechanical setup of the machine, such as sensor locations and distance adjustments, which allow a user to navigate to lower sections for things such as calibration and tracking setup. In order for a user to set or modify the settings for these parameters, a user may use a tap or double tap gesture on a calibrate button 270. In order to return to the main user interface image 110 from the sensor information portion 122 shown in FIG. 13, the user can use a tapping gesture on a return to main screen button 272, which will return the image displayed on the primary touchscreen monitor 98 to the main user interface image 110.

Figure 14:
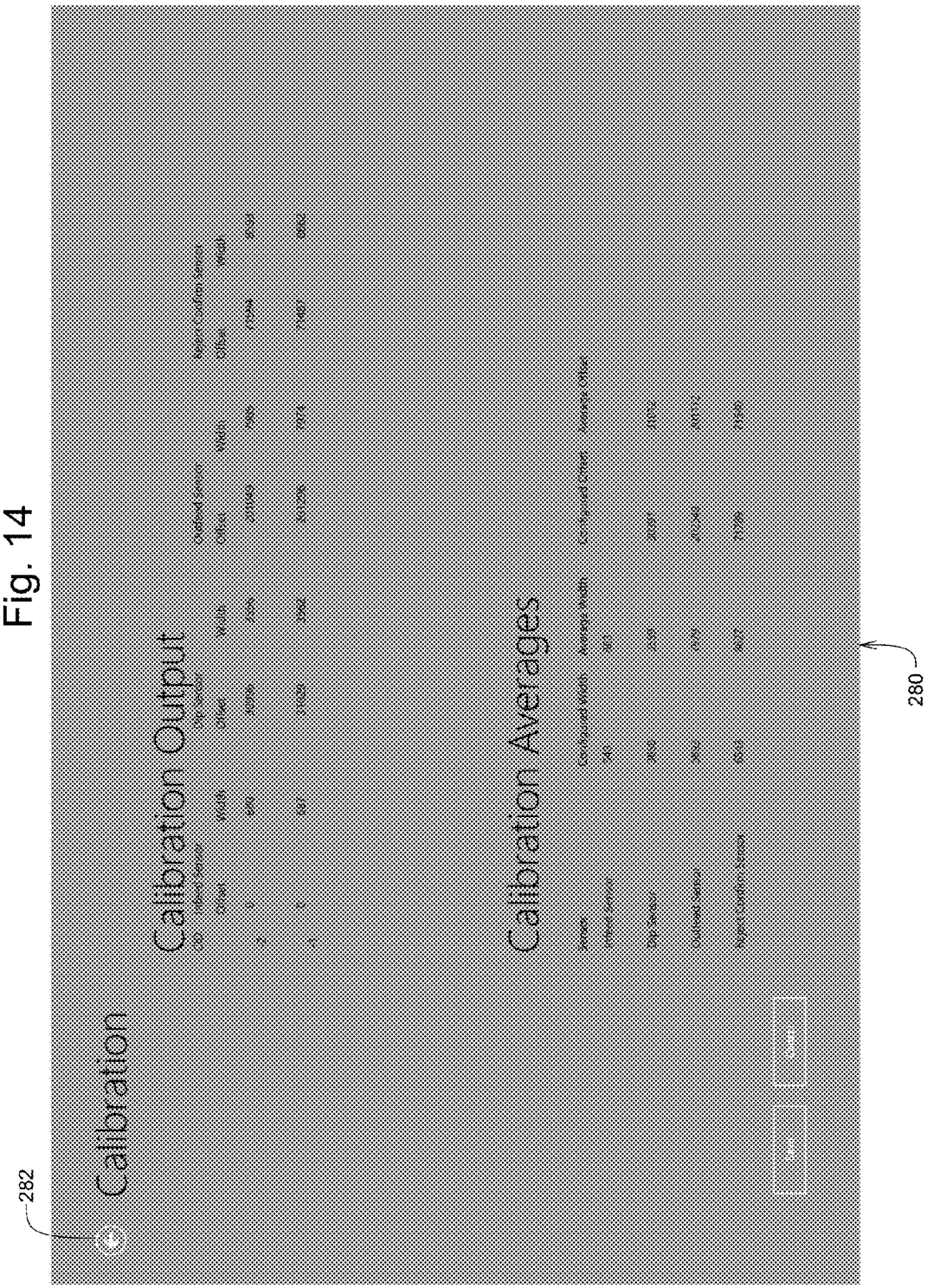
FIG. 14 is a sensor calibration screenshot that is accessible on the touchscreen monitor by selecting the Calibrate button on the enlarged portion of the slidable main user interface screen shown in FIG. 13, which shows information relating to sensor calibration.

By using the calibrate button 270, a calibration image 280 shown in FIG. 14 will be displayed on the touchscreen monitor 98 (shown in FIG. 1). A user can use gestures on the primary touchscreen monitor 98 to bring up editing sections (not shown) to revise the settings shown in the calibration image 280. In order to return to the sensor information portion 122 (shown in FIG. 13) from the calibration image 280 shown in FIG. 14, the user can use a tapping gesture on a return to handling image button 282, which will return the image displayed on the primary touchscreen monitor 98 to the sensor information portion 122.

Figure 15:
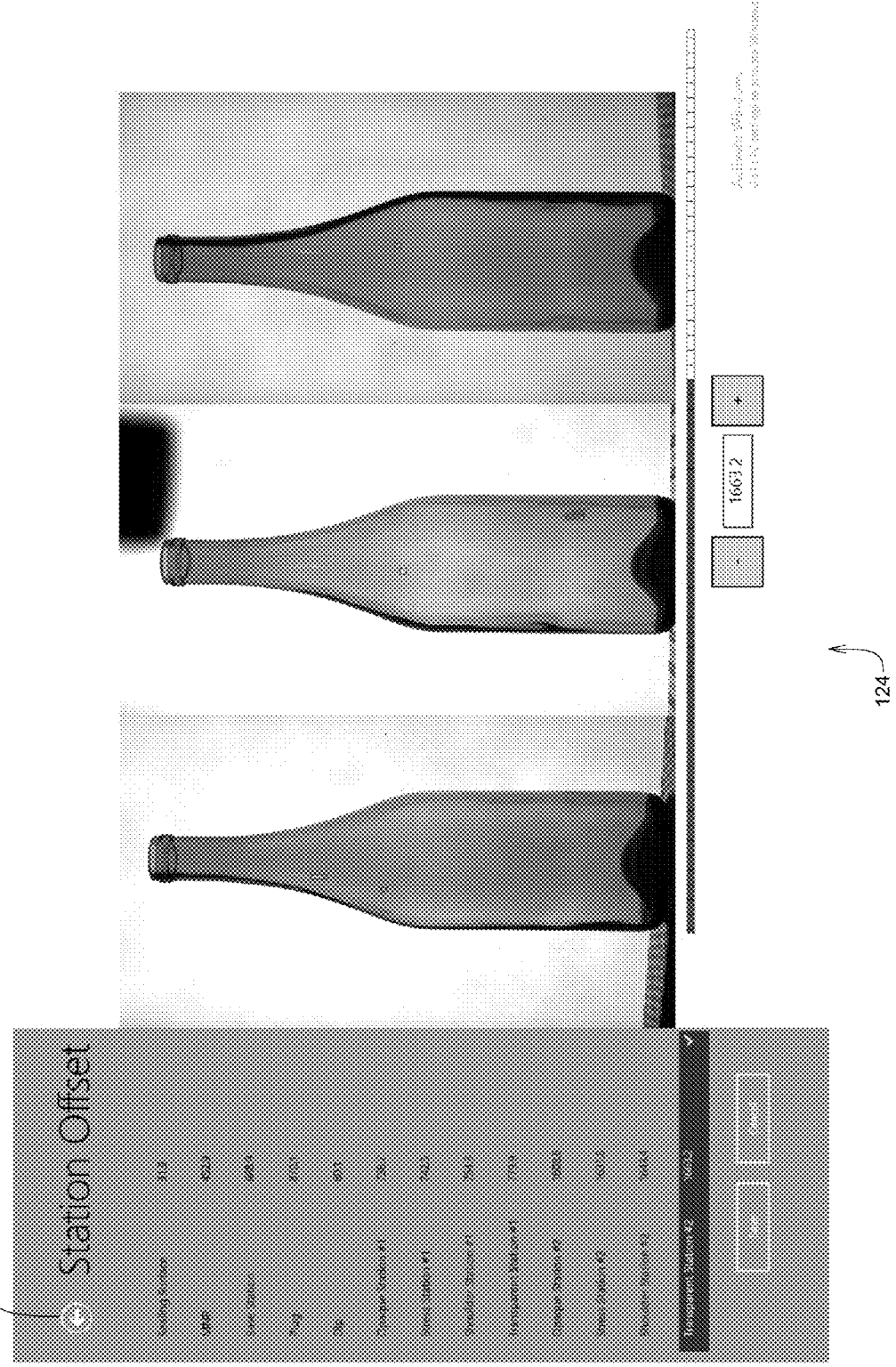
FIG. 15 is an enlarged portion of the slidable main user interface screen shown in FIG. 2 which shows information relating to station offset.

Referring finally to FIG. 15, an enlarged view of the station offset portion 124 of the main user interface image 110 (shown in FIG. 2) which may be accessed by a user by using a tap or double tap gesture on the station offset portion 124 of the main user interface image 110 on the touch-sensitive face of the touchscreen monitor 98 (shown in FIG. 1) is illustrated. The station offset portion 124 shows information relating to station offset, and the parameters shown may be modified by a user using gestures on the primary touchscreen monitor 98 (shown in FIG. 1) to bring up editing sections (not shown) to revise the settings shown in the station offset portion 124. In order to return to the main user interface image 110 from the station offset portion 124 shown in FIG. 14, the user can use a tapping gesture on a return to main screen button 290, which will return the image displayed on the primary touchscreen monitor 98 to the main user interface image 110.

Although the foregoing description of the present invention has been shown and described with reference to particular embodiments and applications thereof, it has been presented for purposes of illustration and description and is not intended to be exhaustive or to limit the invention to the particular embodiments and applications disclosed. It will be apparent to those having ordinary skill in the art that a number of changes, modifications, variations, or alterations to the invention as described herein may be made, none of which depart from the spirit or scope of the present invention. The particular embodiments and applications were chosen and described to provide the best illustration of the principles of the invention and its practical application to thereby enable one of ordinary skill in the art to utilize the invention in various embodiments and with various modifications as are suited to the particular use contemplated. All such changes, modifications, variations, and alterations should therefore be seen as being within the scope of the present invention as determined by the appended claims when interpreted in accordance with the breadth to which they are fairly, legally, and equitably entitled.

While the current application recites particular combinations of features in the claims appended hereto, various embodiments of the invention relate to any combination of any of the features described herein whether or not such combination is currently claimed, and any such combination of features may be claimed in this or future applications. Any of the features, elements, or components of any of the exemplary embodiments discussed above may be claimed alone or in combination with any of the features, elements, or components of any of the other embodiments discussed above.

What is claimed is:

1. A system for inspecting glass containers passing through a glass container inspection machine, comprising:
   a plurality of sensors installed in the glass container inspection machine to inspect glass containers as they pass through the glass container inspection machine and to generate sensor signals indicative of a plurality of sensed parameters of the glass containers;
   at least one processor configured to process the sensor signals received from the plurality of sensors, compare processed sensor signals to predetermined parameters, identify processed sensor signals that vary from the predetermined parameters, and generate image signals that graphically depict glass containers associated with processed sensor signals that vary from the predetermined parameters together with defect information associated with the parameters of such glass containers that vary from the predetermined parameters; and
   at least one touchscreen monitor operatively connected to the at least one processor and configured to display images based upon the image signals and the defect information provided by the at least one processor in a slidable main user interface display larger than a size that can be displayed at any given time on the at least one touchscreen monitor, wherein the at least one touchscreen monitor is configured to be controlled by a user using gestures to slide the slidable main user interface display to access the entirety of the slidable main user interface display;
   wherein the at least one touchscreen monitor and the at least one processor are arranged and configured to allow a user to control the at least one touchscreen monitor using gestures to access and display additional images of glass containers having at least one defect.

2. A system as defined in claim 1, wherein the plurality of sensors are configured to perform inspections of at least five of:
   the sealing surface;
   the base;
   base stress;
   vision plug gauging;
   wire edge;
   vision dip/saddle;
   mold reading;
   opaque sidewall defect;
   dimensional inspection;
   transparent sidewall defect;
   sidewall stress; and
   shoulder inspection.

3. A system as defined in claim 1, wherein the at least one touchscreen monitor is configured to generate gesture data representative of gestures made by a user touching the at least one touchscreen monitor; and wherein the at least one processor is configured to receive and interpret the gesture data and in response to provide image signals to the at least one touchscreen monitor.

4. A system as defined in claim 3, where the at least one touchscreen monitor and the at least one processor are configured to be responsive to gestures a user may provide to the at least one touchscreen monitor include at least:

a fingertip sliding either rightward or leftward, and/or up and down, on the at least one touchscreen monitor to slide an image displayed on the at least one touchscreen monitor from side-to-side and/or or to move an image displayed on the at least one touchscreen monitor image up or down; and pinch-to-zoom gestures to zoom in or out from an image displayed on the at least one touchscreen monitor.

5. A system as defined in claim 1, wherein the at least one processor comprises:

at least one sensor processor configured to process the sensor signals received from the plurality of sensors and to provide the processed sensor signals in response thereto;

a touchscreen processor to operate the at least one touchscreen monitor; and at least one management processor operatively connected to the at least one sensor processor and configured to compare the processed sensor signals to the predetermined parameters, identify processed sensor signals that vary from the predetermined parameters, receive gesture signals indicative of user gestures on the at least one touchscreen monitor, and generate the image signals and provide them to the at least one touchscreen processor.

6. A system as defined in claim 1, wherein the at least one processor is configured to interact with the at least one touchscreen monitor such that when any of a plurality of discrete portions of the slidable main user interface display is displayed on the at least one touchscreen monitor and is accessed by a user gesture on the at least one touchscreen monitor, the at least one processor will operate the at least one touchscreen monitor to display one of a plurality of images each having content respectively associated with one of the plurality of discrete portions of the slidable main user interface display.

7. A system as defined in claim 6, wherein the plurality of images having content respectively associated with one of the plurality of discrete portions of the slidable main user interface display comprise one or more of the following:

a status information image having content providing information relating to the status of the glass container inspection machine;

an recent rejects image having content providing information relating to recently rejected glass containers;

a unified view image having content providing an image of the entirety of a rejected glass container that may be manipulated by user gestures to allow the user to view the rejected glass container from any angle;

an image set image having content providing multiple views of the rejected glass container from the plurality of sensors all contained in a single display larger than a size that can be displayed at any given time on the at least one touchscreen monitor, wherein the entirety of the image set image may be accessed by a user using gestures to slide the image set image to access the entirety of the image set image; and a statistics image having content providing glass container inspection machine statistics.

8. A system as defined in claim 7, wherein the status information image provides content comprising one or more of the following:

a graphical image of the glass container inspection machine depicting any faults and a graphic depiction of the location of the fault in the glass container inspection machine;

a job description image providing a description of the particular glass container being inspected and evaluated;

an event log image providing details including one or more of the glass container inspection machine's health statistics, events, and utilization information such as uptime; and an alarm image providing information related to any alarm events which have recently occurred.

9. A system as defined in claim 8, wherein job description image may be accessed by a user gesture on to display a job list information image configured to allow a user to review information relating to the current job description, review recent job descriptions, and to load or create additional job descriptions.

10. A system as defined in claim 7, wherein the recent rejects image provides content comprising:

one or more of indicators for why a glass container was rejected, the failing sensor results, inspection setup; the time of rejection, the ID of the rejected glass container, and the resulting rejector; and optionally, a single view of a rejected glass container.

11. A system as defined in claim 7, wherein the image set image provides images comprising at least six of the following images:

a sealing surface image;

a base image;

a plug image;

a mold number reader image;

a base stress image;

a dip image 210;

a plurality of opaque images (taken at an angular displacements from each other);

a plurality of stress images (taken at an angular displacements from each other);

a plurality of shoulder images (taken at an angular displacements from each other); and a plurality of plurality of transparent images (taken at an angular displacements from each other).

12. A system as defined in claim 7, wherein the at least one processor is configured to interact with the at least one touchscreen monitor such that when at least one of a particular rejected glass container in the recent rejects image, or the glass container shown in the unified view image, or one of the images in the image set image is accessed by a user gesture on the at least one touchscreen monitor, the at least one processor will operate the at least one touchscreen monitor to display one of a plurality of images of the rejected glass container in a single view image.

13. A system as defined in claim 12, wherein when the single view image is displayed, the user can provide gestures on the at least one touchscreen monitor to operate the at least one touchscreen monitor to individually display each of a plurality of images of the rejected glass container obtained from the plurality of sensors.

14. A system as defined in claim 13, wherein the user can provide gestures on the at least one touchscreen monitor to access an inspection setup image to access and modify a plurality of parameter settings used to determine which glass containers are rejected.

15. A system as defined in claim 6, wherein the plurality of images having content respectively associated with one of the plurality of discrete portions of the slidable main user interface display comprise a calibration image, wherein the user can use gestures on the at least one touchscreen monitor to calibrate the glass container inspection machine.

16. A system for inspecting glass containers passing through a glass container inspection machine, comprising:
    a plurality of sensors installed in the glass container inspection machine to inspect glass containers as they pass through the glass container inspection machine and to generate sensor signals indicative of a plurality of sensed parameters of the glass containers;
    at least one processor configured to process the sensor signals received from the plurality of sensors, compare processed sensor signals to predetermined parameters, identify processed sensor signals that vary from the predetermined parameters, and generate image signals that graphically depict glass containers associated with processed sensor signals that vary from the predetermined parameters together with defect information associated with the parameters of such glass containers that vary from the predetermined parameters; and
    a touchscreen monitor operatively connected to the at least one processor and configured to display images based upon the image signals and the defect information provided by the at least one processor in a slidable main user interface display larger than a size that can be displayed at any given time on the touchscreen monitor, wherein the at least one processor is configured to receive and interpret the gesture data and in response to provide image signals to the at least one touchscreen monitor, and wherein the touchscreen monitor is configured to be controlled by a user using gestures to slide the slidable main user interface display to access the entirety of the slidable main user interface display;
    wherein the touchscreen monitor and the at least one processor are arranged and configured to allow a user to control the touchscreen monitor using gestures to access and display additional images of glass containers having at least one defect; and
    wherein the at least one processor is configured to interact with the at least one touchscreen monitor such that when any of a plurality of discrete portions of the slidable main user interface display is displayed on the at least one touchscreen monitor and is accessed by a user gesture on the at least one touchscreen monitor, the at least one processor will operate the at least one touchscreen monitor to display one of a plurality of images each having content respectively associated with one of the plurality of discrete portions of the slidable main user interface display.

17. A system for inspecting glass containers in a glass container inspection machine, comprising:
    at least one sensor installed in the glass container inspection machine which generates at least one sensor signal indicative of at least one sensed parameter of the glass containers;
    at least one processor configured to process the at least one sensor signal, compare the processed sensor signal to at least one predetermined parameter, identify any processed sensor signal that varies from the predetermined parameter, and generate an image signal that graphically depicts any glass containers associated with a processed sensor signal that varies from the predetermined parameter together with associated defect information; and
    a touchscreen monitor operatively connected to the at least one processor and configured to display an image based upon the image signal and the defect information in a main user interface display larger than a size displayable on the touchscreen monitor, wherein the touchscreen monitor is configured to be controlled by a user using gestures to view the entirety of the main user interface display and to access and display additional images of glass containers having at least one defect.

18. A method for inspecting glass containers passing through a glass container inspection machine, comprising:
    generating sensor signals indicative of a plurality of sensed parameters of glass containers as they pass through the glass container inspection machine to be inspected with a plurality of sensors installed in the glass container inspection machine;
    processing the sensor signals received from the plurality of sensors with at least one processor;
    comparing processed sensor signals to predetermined parameters and identifying processed sensor signals that vary from the predetermined parameters;
    generating image signals that graphically depict glass containers associated with processed sensor signals that vary from the predetermined parameters together with defect information associated with the parameters of such glass containers that vary from the predetermined parameters;
    displaying images associated with the image signals and the defect information provided by the at least one processor on a touchscreen monitor in a slidable main user interface display larger than a size that can be displayed at any given time on the touchscreen monitor;
    controlling the touchscreen in response to a user using gestures to slide the slidable main user interface display to access the entirety of the slidable main user interface display; and
    controlling the touchscreen in response to a user using gestures to access and display additional images of at least one glass container defect having parameters that vary from the predetermined parameters.

19. A method as defined in claim 18, additionally comprising:
    generating gesture data representative of gestures made by a user touching the at least one touchscreen monitor; and
    receiving and interpreting the gesture data with the at least one processor and in response to provide image signals from the at least one processor to the at least one touchscreen monitor.

20. A method as defined in claim 18, additionally comprising:
    when any of a plurality of discrete portions of the slidable main user interface display displayed on the at least one touchscreen monitor is accessed by a user gesture on the at least one touchscreen monitor, operating the at least one touchscreen monitor to display one of a plurality of images each having content respectively associated with one of the plurality of discrete portions of the slidable main user interface display.

* * * * *